US006107045A

United States Patent [19]
Koren et al.

[11] Patent Number: 6,107,045
[45] Date of Patent: Aug. 22, 2000

[54] ANTIBODIES TO LIPOPROTEINS AND APOLIPOPROTEINS AND METHODS OF USE THEREOF

[75] Inventors: Eugen Koren; Mirna Koscec, both of Oklahoma City, Okla.

[73] Assignee: Oklahoma Medical Research Foundation, Oklahoma City, Okla.

[21] Appl. No.: 08/268,809

[22] Filed: Jun. 30, 1994

[51] Int. Cl.[7] ............................. G01N 33/53; C12P 21/08
[52] U.S. Cl. .......................... 435/7.1; 435/7.92; 435/7.95; 435/975; 436/518; 436/524; 436/528; 436/71; 530/387.3; 530/388.1; 530/388.25
[58] Field of Search .......................... 435/7.1, 975, 70.2, 435/70.21, 7.92; 436/530, 518, 528, 536, 540, 547, 548, 71, 524; 530/388.1, 387.3, 388.25

[56] References Cited

U.S. PATENT DOCUMENTS 4,376,110  3/1983  David et al. .
4,786,589  11/1988  Rounds .

FOREIGN PATENT DOCUMENTS 0 257 778 A2  3/1988  European Pat. Off. .
0 407 035 A2  1/1991  European Pat. Off. .
WO 86/05493  9/1986  WIPO .
WO 93/07165  4/1993  WIPO .
WO 93/18067  9/1993  WIPO .

OTHER PUBLICATIONS

Labelle etal, Clinica Chimica Acta, 191:153–160,1990.
Geding, Monoclonal Antibodies:Principles and Practice, 1983 by Academic Press Inc, New York NY pp. 56–97.
Lowman etal, Biochemistry 30: 10832–10838.
Fruchart etal, Clin Chem , 28(1):59–62, 1982.
Marcel etal, J. Lipid Res, 28(7) 768–77, 1987.
Alaupovic, P., et al., "Characterization of Potentially Atherogenic Triglyceride–rich Lipoprotein Particles", *Klin Wochenschr,* 68:38–42 (1990).
Alaupovic, P., et al., "Distribution of Lipoprotein Families in Major Density Classes of Normal Human Plasma Lipoproteins", *Biochim. Biophys. Acta,* 260:689–707 (1972).
Alaupovic, P., et al., "Isolation and Characterization of an apoA–II–Containing Lipoprotein (LP–A–II:B Complex) from Plasma Very Low Density Lipoproteins of Patients with Tangier Disease and Type V Hyperlipoproteinemia",*J. Lipid Res.,* 32:9–19 (1991).
Alaupovic, P., "David Rubinstein Memorial Lecture: The Biochemical and Clinical Significance of the Interrelationship Between Very Low Density and High Density Lipoproteins", *Can. J. Biochem.,* 59:565–579 (1981).
Arntzenius, A.C., "Regression of Atherosclerosis—Benefit can be Expected from Low LDL–C and High HDL–C Levels", *Acta. Cardiol.,* 46:431–438 (1991).
Assmann, G., et al., "The Hypertriglyceridemias: Risk and Management", *Am. J. Cardiol.,* 68(3):1A–4A (1991).

Atmeh, R.F., et al., "Subpopulations of Apolipoprotein A–I in Human High–Density Lipoproteins, Their Metabolic Properties and Response to Drug Therapy", *Biochim. Biophys. Acta,* 751:175–188 (1983).
Avogardo, P., et al., "Are Apolipoproteins Better Discriminators than Lipids for Atherosclerosis?", *Lancet,* 1:901–903 (1979).
Barth, J.D., et al., "Progression and Regression of Atherosclerosis, What Roles for LDL–Cholesterol and HDL–Cholesterol: A Perspective", *Eur. Heart J.,* 12:952–957 (1991).
Blankenhorn, D.H., et al., "Prediction of Angiographic Change in Native Human Coronary Arteries and Aortocoronary Bypass Grafts", *Circulation,* 81(2):479–476 (1990).
Cardin, A.D., et al., "Degradation of Apolipoprotein B–100 of Human Plasma Low Density Lipoproteins by Tissue and Plasma Kallikreins", *J. Biol. Chem.,* 259(13):8522–8528 (1984).
Clackson, Tim, et al., "Making antibody fragments using phage display libraries," *Nature* 352:624–628 (1991).
Curry, M.D., et al., "Determination of Apolipoprotein A and Its Constitutive A–I and A–II Polypeptides by Separate Electroimmunoassays", *Clin. Chem.,* 22(3):315–322 (1976).
Curry, M.D., et al., "Electroimmunoassay, Radioimmunoassay, and Radial Immunodiffusion Assay Evaluated for Quantification of Human Apolipoprotein B", *Clin. Chem.,* 24(2):280–286 (1978).
Curry, M.D., et al., "Determination of Human Apolipoprotein E by Electroimmunoassay", *Biochim. Biophys. Acta,* 439:413–425 (1976).
Curry, M.D., et al., "Quantitative Determination of Human Apolipoprotein C–III by Electroimmunoassay", *Biochim. Biophys. Acta,* 617:503–513 (1980).

(List continued on next page.)

*Primary Examiner*—Patricia A. Duffy
*Attorney, Agent, or Firm*—Arnall Golden & Gregory, LLP

[57] ABSTRACT

Compositions and methods using antibodies which are immunoreactive with specific apolipoproteins to determine the concentrations of lipoproteins such as HDL and LDL, and/or apolipoproteins in human blood, serum or plasma sample, are described. Monoclonal antibodies (MAbs) are described that specifically bind to epitopes present in apolipoproteins and lipoproteins, enabling rapid and reliable determinations of levels of specific blood lipoprotein and/or apolipoprotein levels, including Apo B-100, Apo A-I, Apo A-II, Apo C-III, and Apo E, and thereby determination of relative ratios of HDL and LDL and LpaI and LpaII. In a preferred embodiment, the compositions are strips of a solid phase material coated with one or more of the antibodies and are referred to herein as "dipsticks". The dipsticks specifically bind a lipoprotein or apolipoprotein when dipped into a protein sample. The amount of lipid associated with a bound lipoprotein or the amount of apolipoprotein bound on the dipstick is quantitated using an appropriate method, for example, by staining with a lipid stain or reaction with a second labelled antibody. The intensity of the stain on the dipstick is proportional to the concentration of the lipoprotein lipid or apolipoprotein circulating in the blood and can be quantitated by comparison with standards containing known amounts of lipid.

31 Claims, No Drawings

OTHER PUBLICATIONS

Cwirla, Steven E., et al., "Peptides on phage: A vast library of peptides for identifying ligands," *Proc. Natl. Acad. Sci. USA* 87:6378–6382 (1990).

Friedewald, W.T., et al., "Estimation of the Concentration of Low–Density Lipoprotein Cholesterol in Plasma, Without Use of the Preparative Ultracentrifuge", *Clin. Chem.*, 18(6):499–502 (1972).

Fruchart, J.E., et al., "Apolipoprotein A–Containing Lipoprotein Particles: Physiological Role, Quantification, and Clinical Significance", *Clin. Chem.*, 38(6):793–797 (1992).

Galeano, N.F., et al., *J. Biol. Chem.*, "Apoprotein B Structure and Receptor Recognition of Triglyceride–rich Low Density Lipoprotein (LDL) is Modified in Small LDL but Not in Triglyceride–rich LDL of Normal Size", 269(1):511–519 (1994).

Galfré, G., et al., "Preparation of Monoclonal Antibodies: Strategies and Procedures", *Methods Enzymol.*, 73:3–46 (1981).

Glenner, G.G., "Formazans and Tetrazolium Salts", In: *H.J. Conn's Biological Stains,* The Williams and Wilkins Company, USA, 225–235 (1990).

Gordon, T., et al., "High Density Lipoprotein as a Protective Factor Against Coronary Heart Disease", *Am. J. Med.*, 62:707–714 (1977).

Harduin, P., et al., "Modulation of the Expression of Human LDL–Apo B–100 Epitopes by Lipids and Apolipoproteins", *Arterioscl. Thromb.*, 13(4):529–535 (1993).

Holliger, P., et al., "'Diabodies': Small bivalent and Bispecific Antibody Fragments", *Proc. Natl. Acad. Sci. USA,* 90:6444–6448 (1993).

Hoogenboom, H.R., et al., "Multi–Subunit Proteins on the Surface of Filamentous Phage: Methodologies for Displaying Antibody (Fab) Heavy and Light Chains", *Nucl. Acids Res.,* 19(15):4133–4137 (1991).

Ito, W., et al., "Development of an Artificial Antibody System with Multiple Valency Using an Fv Fragment Fused to a Fragment of Protein A", *J. Biol. Chem.,* 268(27):20668–20675 (1993).

Kane, J.P., "Characterization of Apolipoprotein B–Containing Lipoproteins", *Method. Enzymol.,* 129:123–129 (1986).

Kashyap, M.L., et al., "Radioimmunoassay of Human Apolipoprotein CII—A Study in Normal and Hypertriglyceridemic Subjects", *J. Clin. Invest.,* 60:171–180 (1977).

Keidar, S., et al., "A High Carbohydrate–Fat Free Diet Alters the Proportion of Heparin–Bound VLDL in Plasma and the Expression of VLDL–ApoB–100 Epitopes", *Metabolism,* 39(3):281–288 (1990).

Koren, E., et al., "Isolation and Characterization of Simple and Complex Lipoproteins Containing Apolipoprotein F from Human Plasma", *Biochemistry,* 21:5347–5351 (1982).

Koren, E., et al., "Apolipoprotein A–I and Apolipoprotein B Containing Lipoprotein Particles in Coronary Patients Treated with Extracorporal Low Density Lipoprotein Precipitation (HELP)", *Atherosclerosis,* 95:157–170 (1992).

Koren, E., et al., "Characterization of a Monoclonal Antibody that Binds Equally to All Apolipoprotein and Lipoprotein Forms of Human Plasma Apolipoprotein B. I. Specificity and Binding Studies", *Biochim. Biophys. Acta,* 876:91–100 (1986).

Koren, E., et al., "Characterization of a Monoclonal Antibody that Binds Equally to All Apolipoprotein and Lipoprotein Forms of Human Plasma Apolipoprotein B. II. Isolation of Apolipoprotein B–Containing Lipoproteins from Human Plasma", *Biochim. Biophys. Acta,* 876:101–107 (1986).

Koren, E., et al., "Use of 'Pan' Monoclonal Antibody for Quantification of Apolipoprotein A–II", *Arteriosclerosis,* 6:521a (1986).

Koren, E., et al., "Quantification of Two Different Types of Apolipoprotein A–I Containing Lipoprotein Particles in Plasma by Enzyme–Linked Differential–Antibody Immunosorbent Assay", *Clin. Chem.,* 33(1):38–43 (1987).

Krauss, R.M., "Relationship of Intermediate and Low–Density Lipoprotein Subspecies to Risk of Coronary Artery Disease", *Am. Heart J.,* 113(2):578–582 (1987).

Krodel, E., et al., "Technical Challenges in the Development of the CIBA Corning ACS:180 Benchtop Immunoassay Analyzer", In: *Bioluminescence and Chemiluminescence: Current Status.* John Wiley and Sons Inc., New York, 107–110 (1991).

Kuyl, J.M., et al., "Observed Relationship Between Ratios HDL–Cholesterol/Total Cholesterol and Apolipoprotein A1/Apolipoprotein B", *Clin. Biochem.,* 25:313–316 (1992).

Kwiterovich, P.O., Jr., et al., "Prevalence of Hyperapobetalipoproteinemia and Other Lipoprotein Phenotypes in Men (Aged $\leq$50 Years) and Women ($\leq$60 Years) With Coronary Artery Diseases", *Am. J. Cardiol.,* 71:631–639 (1993).

Kwiterovich, P.O., Jr., et al., "Comparison of the Plasma Levels of Apolipoprotein B and A–1, and Other Risk Factors in Men and Women with Premature Coronary Artery Disease", *Am. J. Cardiol.,* 69:1015–1021 (1992).

La Belle, M., et al., "Increased Immunoreactivity of Apolipoprotein B Epitopes During Prolonged Storage of Low Density Lipoproteins", *Clin. Chim. Acta,* 191: 153–160 (1990).

Lee, D.M., et al., "Properties of Apolipoprotein B in Urea and in Aqueous Buffers—The Use of Glutathione and Nitrogen in its Solubilization", *Biochim. Biophys. Acta,* 666:133–146 (1981).

Lopes–Virella, M.F., et al., "Cholesterol Determination in High–Density Lipoproteins Separated by Three Different Methods", *Clin. Chem.,* 23:(5):882–884 (1977).

Lowman, Henry B., et al., "Selecting High–Affinity Binding Proteins by Monovalent Phage Display," *Biochemistry* 30:10832–10838 (1991).

Maciejko, J.J., et al., "Apolipoprotein A–I as a Marker of Angiographically Assessed Coronary–Artery Disease", *N. Engl. J. Med.,* 309(7):385–389 (1983).

McGill, D.A., et al., "Relationship of Blood Cholesterol and Apoprotein B Levels to Angiographically Defined Coronary Artery Disease in Young Males", *Coron. Artery Dis.,* 4(3):261–270 (1993).

Mézes. P., "Construction and Biodistribution Studies of Multivalent Single–Chain Antibodies", Construction and Biodistribution Studies of Multivalent Single–Chain Antibodies, *The Fourth Annual IBC International Conference on Antibody Engineering,* Dec. 1993, Coronado, CA.

Miller, N.E., et al., "High–Density Lipoprotein and Coronary Heart–Disease: A Prospective Case–Control Study", *Lancet,* 1:965–968 (1977).

Miller, G.J., et al., "Plasma–High–Density–Lipoprotein Concentration and Development of Ischaemic Heart–Disease", *Lancet,* 1:16–19 (1975).

Milne, R., et al., "The Use of Monoclonal Antibodies to Localize the Low Density Lipoprotein Receptor–Binding Domain of Apolipoprotein B", *J. Biol. Chem.*, 264(33):19754–19760 (1989).

Mulder, K., et al., "An Evaluation of Three Commercial Methods for the Determination of LDL–Cholesterol", *Clin. Chim. Acta*, 143:29–35 (1984).

Olofsson, S–O, et al., "Isolation and Partial Characterization of a Polypeptide Belonging to Apolipoprotein B from Low–Density Lipoproteins of Human Plasma", *Biochemistry*, 19:1059–1064 (1980).

Ortolá, J., et al., "Biological Variation Data Applied to the Selection of Serum Lipid Ratios used as Risk Markers of Coronary heart Disease", *Clin. Chem.*, 38(1):56–59 (1992).

Osborne, J.D., et al., "The Plasma Lipoproteins", *Adv. Prot. Chem.*, 31:253–337 (1977).

Parham, P., "Handbook of Experimental Immunology, vol. 1: Immunochemistry", Weir, D.M., Editor, Blackwell Scientific Publications, Oxford (1986).

Parmley, S.F., et al., "Filamentous Fusion Phage Cloning Vectors for the Study of Epitopes and Design of Vaccines", *Adv. Exp. Med. Biol.*, 251:215–218 (1989).

Puchois, P., et al., "Apolipoprotein A–I Containing Lipoproteins in Coronary Artery Disease", *Atherosclerosis*, 68:35–40 (1987).

Savage, M.D., et al., "Avidin–Biotin Chemistry: A Handbook," Pierce Chemical Company, Rockford, IL (1992).

Smith, L.C., et al., "The Plasma Lipoproteins: Structure and Metabolism", *Ann. Rev. Biochem.*, 47:751–777 (1978).

Sniderman, A., et al., Association of Coronary Atherosclerosis with Hyperapobetalipoproteinemia [Increased Protein but Normal Cholesterol Levels in Human Plasma Low Density (β) Lipoproteins], *Proc. Natl. Acad. Sci. USA*, 77(1):604–608 (1980).

Socorro, L., et al., "Preparation and Properties of Soluble, Immunoreactive apoLDL", *G.J. Lipid Res.*, 20:631–638 (1979).

Stein, E.A., et al., "Lipids, Lipoproteins, and Apolipoprotein", In *Tietz Textbook of Clinical Chemistry*, W.B. Saunders, Philadelphia, 1002–1093 (1994).

Tornvall, P., et al., "Relation of Plasma Levels and Composition of Apolipoprotein B–Containing Lipoproteins to Angiographically Defined Coronary Artery Disease in Young Patients With Myocardial Infarction", *Circulation*, 88:2180–2189 (1993).

Warnick, G.R., et al., "Dextran Sulfate–$Mg^{2+}$ Precipitation Procedure for Quantitation of High–Density–Lipoprotein Cholesterol", *Clin. Chem.*, 28(6):1379–1388 (1982).

Weeks, I., et al., "Two–Site Immunochemiluminometric Assay for Human $\alpha_1$–Fetoprotein", *Clin. Chem.*, 29(8):1480–1483 (1983).

Wood, P., "Heterogeneous Fluorimmunoassay", *Principles and Practice of Immunoassay*, Stockton Press, New York, 365–392 (1991).

"Report of the Working Group on Atherosclerosis of the National Heart and Lung and Blood Institute", 2 (Washington, D.C.: Government Printing Office, 1981) DHEW Publication No. (NIH) 82–2035).

The Lipid Research Clinics Coronary Primary Prevention Trial Results: II, *JAMA*, 251:365–374 (1984).

"Report of the Expert Panel on Blood Cholesterol Levels in Children and Adolescents", *Pediatrics*, 89:525–584 (1992).

"Report of the National Cholesterol Education Program Expert Panel on Detection, Evaluation and Treatment of High Blood Cholesterol in Adults," *Arch. Intern. Med.* 148:36–69 (1988).

ANTIBODIES TO LIPOPROTEINS AND APOLIPOPROTEINS AND METHODS OF USE THEREOF

BACKGROUND OF THE INVENTION

This invention is generally in the field of methods and compositions for the determination and quantitation of lipoproteins and apolipoproteins in human blood.

Human Plasma Lipoproteins and Apolipoproteins

Plasma lipoproteins are carriers of lipids from the sites of synthesis and absorption to the sites of storage and/or utilization. Lipoproteins are spherical particles with triglycerides and cholesterol esters in their core and a layer of phospholipids, nonesterified cholesterol and apolipoproteins on the surface. They are categorized into five major classes based on their hydrated density as very large, triglyceride-rich particles known as chylomicrons (less than 0.95 g/ml), very low density lipoproteins (VLDL, 0.95 to 1.006 g/ml), intermediate-density lipoproteins (IDL, 1.006 to 1.019 g/ml), low-density lipoproteins (LDL, 1.019 to 1.063 g/ml) and, high-density lipoproteins (HDL, 1.063 to 1.210 g/ml). Plasma lipoproteins can be also classified on the basis of their electrophoretic mobility. HDL comigrate with $\alpha$-globulins, LDL with $\beta$-globulins, VLDL between $\alpha$- and $\beta$-globulins with so called pre-$\beta$ globulins, whereas chylomicrons remain at the point of application. (Osborne, J. D. and Brewer, B. Jr. *Adv. Prot. Chem.* 31:253–337 (1977); Smith, L. C. et al. *Ann. Rev. Biochem.,* 47:751–777 (1978)).

Apolipoproteins are protein components of lipoproteins with three major functions: (1) maintaining the stability of lipoprotein particles, (2) acting as cofactors for enzymes that act on lipoproteins, and (3) removing lipoproteins from circulation by receptor-mediated mechanisms. The four groups of apolipoproteins are apolipoproteins A (Apo A), B (Apo B), C (Apo C) and E (Apo E). Each of the three groups A, B and C consists of two or more distinct proteins. These are for Apo A: Apo A-I, Apo A-II, and Apo A-IV, for Apo B: Apo B-100 and Apo B-48; and for Apo C: Apo C-I, Apo C-II and Apo C-III. Apo E includes several isoforms.

Each class of lipoproteins includes a variety of apolipoproteins in differing proportions with the exception of LDL, which contains Apo B-100 as a sole apolipoprotein. Apo A-I and Apo A-II constitute approximately 90 percent of the protein moiety of HDL whereas Apo C and Apo E are present in various proportions in chylomicrons, VLDL, IDL and HDL. Apo B-100 is present in LDL, VLDL and IDL. Apo B-48 resides only in chylomicrons and so called chylomicron remnants (Kane, J. P., *Method. Enzymol.* 129:123–129 (1986)).

Lipoprotein metabolism is a very complex process involving exogenous and endogenous pathways as well as a reverse cholesterol transport. In the exogenous pathway, the triglycerides and cholesterol from an individual's diet are incorporated into chylomicrons which enter into the blood stream via intestinal lymph. Lipoprotein lipase hydrolyzes the triglyceride component of chylomicrons into free fatty acids which are taken up by muscle cells and/or adipocytes. As the triglyceride core of chylomicrons is depleted, chylomicron remnant particles are formed and removed from the circulation via chylomicron remnant receptor present on the surface of hepatic cells.

In the endogenous pathway, the liver synthesizes triglycerides and cholesterol. The endogenously made triglycerides and cholesterol are packed into triglyceride rich VLDL particles and secreted into the circulation. Once in the blood, most of the triglyceride content of VLDL particles is hydrolyzed by lipoprotein lipase, releasing free fatty acids to be used as a source of energy or for storage. As a result of this process, VLDL particles diminish in size and increase in density and are converted into VLDL remnants or IDL. Further processing includes additional lipolysis and exchange of lipids and apolipoproteins between IDL and HDL, leading to the formation of LDL which contain mostly cholesterol esters in the core and phospholipids and Apo B-100 on the surface. LDL particles are taken up by the hepatic and extrahepatic cells via specific LDL-receptor.

The reverse cholesterol transport pathway starts with the secretion of nascent HDL particles which are produced by the liver and intestine. These disk-like particles consist primarily of phospholipids surrounded by Apo A-I. They accept free cholesterol from peripheral tissues which is esterified and translocated into the core of HDL particles, which become spherical and ready to deliver their cholesterol content to hepatocytes. During the degradation of VLDL and LDL, HDL particles also accept free cholesterol and apolipoproteins from these lipoproteins.

Role of Lipoproteins in Atherosclerosis

Atherosclerosis is a chronic disease characterized by progressive deposition of cholesterol, fibrous elements and minerals in arterial walls. Atherosclerosis is the underlying pathophysiological process of coronary heart disease (CHD), one of the leading causes of death in Western World (*Report of the Working Group on Atherosclerosis of the National Heart and Lung and Blood Institute,* 2 (Washington, D.C.: Government Printing Office, 1981) DHEW Publication No. (NIH) 82-2035). Although development of CHD is a very complex process influenced by many contributing factors, subintimal cholesterol deposition in coronary arteries is one of the earliest and most important events during the course of disease. The major source of cholesterol found in arterial wall deposits is plasma lipoproteins. Because of their diverse metabolic roles and properties, lipoproteins associate differently with the risk of developing CHD.

LDL particles constitute approximately two-thirds of total cholesterol (TC) and form the primary atherogenic fraction of the serum cholesterol. Many epidemiological and clinical studies have shown that increased LDL levels in the blood are associated with an increased risk of CHD. For example, the results of the Lipid Research Clinics trial have shown that reduction of LDL-cholesterol (LDL-C) is associated with a significant decrease in CHD incidence (The Lipid Research Clinics Coronary Primary Prevention Trial results:II. *JAMA* 251:365–374 (1984)).

The evidence relating CHD and triglyceride-rich lipoproteins such as VLDL is not as strong as for the LDL. Many studies have shown a positive correlation between elevated serum triglyceride levels and increased risk of CHD. However, the independent link between elevated serum triglyceride (TG) and CHD breaks down when multivariate analyses are used to control statistically for the effects of total cholesterol (TC) and HDL-cholesterol (HDL-C). These observations suggest that increased CHD risk noted in patients with hypertriglyceridemia could be due to either the accumulation of triglyceride-rich particles that are uniquely atherogenic in some people or to the association with reduced HDL-C (Assmann, G. et al.,*Am. J. Cardiol.,* 68:1–3 (1991)). Remnants of triglyceride-rich particles, (for example, chylomicron and VLDL remnants) which are found in IDL are also atherogenic (Krauss, R. M.,*Am. Heart J.,* 112:578–582 (1987)).

In contrast to the atherogenic potential of LDL, VLDL and VLDL remnants, HDL are inversely correlated with CHD, so that individuals with low concentrations of HDL-C have an increased incidence of CHD (Gordon, T. et al., *Am. J. Med.,* 62:707–714 (1977); Miller, N. E. et al., *Lancet,* 1:965–968 (1977); Miller, G. J. and Miller, N. E., Lancet, 1:16–19 (1975)). At the other extreme, individuals with high concentrations of HDL, such as found in familial hyperalphalipoproteinemia, seldom express symptoms of CHD. The fact that pre-menopausal females have higher HDL concentrations and less CHD compared to males, also supports the anti-atherogenic role of HLD. Furthermore, postmenopausal women have a significant increase in CHD risk while their HDL concentrations decrease.

Measurement of LDL

LDL consists of a hydrophobic lipid core composed of cholesterol esters and triglycerides. The lipid core of the LDL particle is surrounded by an amphipathic coat composed of phospholipids, unesterified cholesterol and Apo B. Each LDL particle contains one molecule of Apo B-100. On a weight basis, LDL is composed of 38 percent cholesterol ester, 22 percent phospholipid, 21 percent protein, 11 percent triglyceride and 8 percent unesterified cholesterol.

Accurate measurements of LDL using presently available technology depends on separation of LDL particles from other lipoproteins. Once the LDL particles are separated, their concentration can be quantified by determination of their cholesterol (LDL-C) or Apo B (LDL-B) content. LDL-C is the most commonly used parameter.

Several ultracentrifugation methods have been developed over the years to separate serum lipoproteins. Analytical ultracentrifugation was developed in the 1950s and continues to be used today in some research laboratories. In this technique, lipoproteins are separated by analytical ultracentrifugation and quantitated by optical refraction. This method of quantitation measures lipoprotein mass, but does not give any information about lipid or protein composition. Sequential ultracentrifugation was developed in 1955 to overcome some of the limitations of analytical ultracentrifugation. In this technique, lipoproteins are separated by repeated ultracentrifugations after progressively increasing the sample density. Lipoproteins can be isolated within any desired density interval and in sufficient quantities to allow for multiple chemical analyses. Sequential ultracentrifugation continues to be used today for preparative isolation of lipoproteins. However, the ultracentrifugation methods are too expensive and time consuming for the purpose of measuring LDL-C levels to assess lipoprotein abnormalities and CHD risk in routine clinical application. Other methods for separating LDL include size-exclusion and other types of chromatography, electrophoresis, and precipitation. The size-exclusion chromatography methods include agarose column chromatography and high-performance gel filtration column chromatography. The time required for analysis, typically 24 hours, is the major difficulty with agarose column chromatography. The development of high-performance liquid chromatography (HPLC) methods has reduced the analysis time, but has increased the cost and complexity of the procedure. Affinity chromatography using anti-LDL antibodies, heparin, or dextran sulfate linked to SEPHAROSE™ (Pharmacia LKB, Piscataway, N.J.) gels has also been used to isolate LDL.

Electrophoresis methods, which separate lipoproteins according to their charge in addition to size, have been used in many clinical laboratories. This technique is helpful in qualitative assessment of various types of hyperlipoproteinemias. Agarose gel electrophoresis at pH 8.6, followed by visualization using lipophilic stains such as Oil Red O, Sudan Black B or Sudan Red 7B, have been commonly used with commercial reagents packaged as kits, for example, as sold by Ciba Corning (Medfield, Mass.) Lipoprotein concentrations are then estimated by densitometry based on the color intensity of the separated bands.

Several methods for selective chemical precipitation of LDL have been described and commercialized (Mulder, K. et al., *Clin. Chim. Acta* 143:29–35 (1984)). The precipitation methods, which quantitate LDL-C as the difference between the total cholesterol and the sum of VLDL- and HDL-cholesterol (Friedewald, W. T. et al., *Clin. Chem.* 18:499–502 (1972)), are precise and produce reasonably accurate results relative to ultracentrifugation methods when serum TG values are low. However, most investigators have found that the precipitation methods are plagued with systematic errors when samples with high TG levels are analyzed.

Most recently, a method was developed which uses latex beads coated with affinity-purified polyclonal goat antisera directed against apolipoproteins in HDL and VLDL (Sigma, St. Louis, Mo.). In this method, a plasma or serum sample is incubated with the beads for 5 to 10 minutes at room temperature and then centrifuged for 5 minutes to remove the HDL and VLDL bound to the beads. The remainder of the sample is then assayed for cholesterol using a standard enzymatic cholesterol assay (Sigma St. Louis, Mo.) to obtain a value for the LDL-C, the presumed remaining source of cholesterol in the sample.

Techniques used for measurement of LDL by its Apo B content include radioimmunoassay; enzyme immunoassay (ELISA competitive or capture systems), fluorescence immunoassay, radial immunodiffusion, nephelometry, turbidimetry and electroimmunoassay.

The National Cholesterol Education Program (NCEP) recommended the determination of LDL-C concentration in diagnosis and treatment of hypercholesterolemia. According to NCEP, concentrations lower than 130 mg/dl in adults are considered desirable, concentrations between 130 and 150 mg/dl are borderline high, and concentrations above 160 md/dl are high (see Report of the National Cholesterol Education Program Expert Panel on Detection, Evaluation and Treatment of High Blood Cholesterol in Adults, *Arch. Intern. Med.* 148:36–69 (1988)). The NCEP also recommended determining LDL-cholesterol concentrations for children and adolescents since the high LDL correlates with the extent of coronary and aortic atherosclerosis in this age group as well as development of CHD later in life. Cholesterol values of 110 mg/dl are desirable, values between 110 and 129 mg/dl are borderline high, and values above 130 mg/dl are considered high in children and adolescents (see Report of the Expert Panel on Blood Cholesterol Levels in Children and Adolescents, Pediatrics 89:525–584 (1992)).

Measurement of HDL

HDL, the smallest in size of the lipoproteins, includes a family of lipoprotein particles that exist in a constant state of dynamic flux as they interact with LDL, IDL and VLDL. HDL have the highest proportion of protein (50 percent) relative to lipid compared to other lipoproteins. The major HDL proteins are Apo A-I and Apo A-II, with lower concentrations of Apo C(I,II & III), E, and A-IV. Phospholipids are the principal lipid component of HDL, with cholesterol esters, unesterified cholesterol, and TG present in lower concentrations.

As in the case of LDL, HDL is typically measured after its separation from other lipoproteins and quantification of cholesterol in the HDL (HDL-C). As described above, the separation of HDL can be accomplished by ultracentrifugation, chromatographic procedures, electrophoresis and precipitation. The reliability of lipoprotein quantitations following separation by ultracentrifugation techniques depends upon both the performance of the analytical quantitation method, such as cholesterol analysis, and the skills of the technologist in performing accurate recovery and transfer of the lipoprotein fractions from the ultracentrifuge tube. HDL-C is more easily quantitated by selective precipitation techniques compared to either ultracentrifugation or electrophoretic methods. Currently, the majority of clinical laboratories use either dextran sulfate or sodium phosphotungstate procedures for HDL-C analysis (Warnick, G. R. et al., *Clin. Chem.* 28:1379–1388 (1982); Lopes-Virella, M. F. et al., Clin. Chem. 23:882–884 (1977)). According to NECP guidelines, patients with HDL-C levels below 35 mg/dl are considered to be at risk for CHD.

LDL/HDL Ratio

Some studies have demonstrated that the ratio between LDL-C and HDL-C represents a better predictor of CHD than either of these two parameters alone (Arntzenius, A. C., *Acta. Cardiol.,* 46:431–438 (1991); Barth J. D. and Arntzenius, A. C., *Eur. Heart J.,* 12:952–957 (1991); Ortola, J. et al., *Clin. Chem.,* 38:56–59 (1992); Gohlke H., *Wien Klin. Wochenschr.,* 104:309–313 (1992)).

LPA-I and LPA-I:A-II Lipoprotein Particles There are two subpopulations of HDL lipoprotein particles known as LPA-I and LPA-I:A-II (Koren, E. et al. *Clin. Chem.,* 33:38–43 (1987)). LPA-I particles contain Apo A-I but no Apo A-II while LPA-I:A-II particles contain both apolipoproteins. These HDL subpopulations can be measured by enzyme immunoassay (Koren, E. et al. *Clin. Chem.,* 33:38–43 (1987)) or electroimmunoassay (Atmeh, R. F. et al., *Biochim. Biophys. Acta,* 751:175–188 (1983)). Their importance has been emphasized by several studies which demonstrated that LPA-I is a more active component in reverse cholesterol transport and, therefore, more antiatherogenic than other lipoproteins (Puchois, P. et al., *Atherosclerosis,* 68:35–40 (1987); Fruchart, J. C. and Ailhaud, G., *Clin. Chem.,* 38:793–797 (1992)).

Measurements of VLDL. IDL, C-III and E Ratios

Triglyceride-rich VLDL as well as their remnants (IDL) can be separated by the above ultracentrifugational, chromatographic and electrophoretic methods and quantified by determination of their cholesterol content. Although atherogenic, these lipoprotein particles are not commonly measured in routine clinical laboratories. Instead, serum triglyceride concentration in the fasting state is considered representative of the VLDL content and is used traditionally in the assessment of the VLDL-related CHD risk. More recently, measurements of the so-called C-III and E ratios have been proposed as reliable predictors of the VLDL-related CHD risk. The principle of these measurements is to precipitate all Apo B-100-containing particles (VLDL, IDL and LDL) with heparin which leaves HDL in the heparin supernate. This separation is followed by an immunochemical determination of Apo C-III or Apo E in the heparin precipitate and heparin supernate and calculation of the corresponding ratios by dividing C-III or E concentration in heparin supernate with their respective concentrations in heparin precipitate (Alaupovic, P., *Can. J. Biochem.,* 59:565–579 (1981)). Most of the Apo C-III and Apo E in the heparin precipitate is associated with Apo B in VLDL and VLDL remnant (IDL) particles. The C-III and E in the heparin supernate is associated with Apo A-I in HDL particles. Apo C-III and/or Apo E in the heparin precipitate reflects the concentration of VLDL and VLDL-remnant particles both of which are atherogenic. The Apo C-III and Apo E in the heparin supernate represents HDL particles which are anti-atherogenic. Therefore, a low C-III and E ratio is associated with increased risk of CHD because it reflects either high VLDL and IDL and normal HDL or, more frequently, high VLDL and IDL combined with low HDL. In fact, the predictive power of C-III ratio has surpassed that of triglycerides in several clinical studies (Alaupovic, P. and Blankenhorn, D. H., *Klin. Wochenschr.,* 60:38–40 (1990); Blankenhorn, D. H. et al., *Circulation* 81:470–478 (1990)).

Measurements of Apo A-I and B

Apo B-100 is an integral component of the four major atherogenic lipoproteins: VLDL, IDL, LDL and Lp(a). Apo B-100 is distinguished from Apo B-48, which is found only in lipoproteins of intestinal origin, such as chylomicrons and chylomicron remnants. Apo B-48 is usually undetectable in the systemic circulation, except in rare subjects with Type I, III, or V hyperlipidemia. Apo B's initial function in VLDL and IDL appears to be structural; however, with exposure of binding domains on LDL, it becomes responsible for interaction with high-affinity LDL receptors on cell surfaces, which results in uptake and removal of LDL from the circulation. Several studies have shown that an increased Apo B level in blood is a reliable marker for coronary atherosclerosis (Sniderman, A. et al., *Proc. Natl. Acad. Sci. USA,* 77:604–608 (1980); Kwiterovich, P. O. et al., *Am. J. Cardiol.,* 71:631–639 (1993); McGill et al. *Coron. Artery Dis.,* 4:261–270 (1993); Tornvall, P. et al., *Circulation,* 88:2180–2189 (1993)).

Apo A-I is the major protein constituent of lipoproteins in the high density range. Apo A-I may also be the ligand that binds to a proposed hepatic receptor for HDL removal. A number of studies support the clinical sensitivity and specificity of Apo A-I as a negative risk factor for atherosclerosis (Avogaro, P. et al., *Lancet,* 1:901–903 (1979); Maciejko, J. J. et al., *N. Enql. J. Med.,* 309:385–389 (1983)). Some investigators have also described Apo A-I/Apo B ratio as a useful index of atherosclerotic risk (Kwiterovich, P. O. et al., *Am. J. Cardiol.,* 69:1015– 1021 (1992); Kuyl, J. M. and Mendelsohn, D., *Clin. Biochem.,* 25:313–316 (1992)).

Techniques used for both Apo A-I and B are confined to immunological procedures using antibodies directed against Apo A-I or B and include radioimmunoassay (RIA), enzyme immunoassay (ELISA), competitive or capture systems, fluorescence immunoassay, radial immunodiffusion, nephelometry, turbidimetry and electroimmunoassay.

To summarize, there are several lipoprotein related parameters that are currently used as predictors of CHD. Some of them represent atherogenic lipoproteins (total cholesterol, triglycerides, LDL, IDL, VLDL, Lp(a) and Apo B and are positively associated with CHD whereas the others are antiatherogenic factors, HDL, Apo A-I and LPA-I which are inversely related to the disease. The ratios of some of these parameters, such as LDL/HDL, Apo A-I/Apo B, C-III and E ratio, appear to be even more sensitive predictors of CHD because each of them reflects both anti-atherogenic and atherogenic factors in a single parameter.

All of the methods currently used to determine lipoprotein related risk factors require a laboratory with the necessary equipment and trained personnel to carry out each of the technical steps, to perform the necessary calculations and to interpret the results. The only exception is a new total cholesterol measurement device (AccuMeter Cholesterol Self-Test) developed by ChemTrack (Sunnyvale, Calif.) and designed for home use. However, a total cholesterol level is a less sensitive predictor compared to the levels of specific lipoproteins, apolipoproteins or ratios thereof.

It is therefore an object of the present invention to provide methods and means to rapidly and reliably determine levels of specific lipoproteins, apolipoproteins or the ratios thereof in whole blood, serum or plasma without the necessity of laboratory equipment or technically trained personnel.

It is another object of the present invention to provide antibodies immunoreactive with specific epitopes on lipoproteins, such as those on LDL, VLDL and HDL, that enable rapid and reliable determinations of levels of lipoproteins and/or apolipoproteins in whole blood, serum or plasma.

SUMMARY OF THE INVENTION

Compositions and methods using antibodies which are immunoreactive with specific apolipoproteins to determine the concentrations of lipoproteins such as HDL and LDL, and/or apolipoproteins in human blood, serum or plasma sample, are described. Monoclonal antibodies (MAbs) are described that specifically bind to epitopes present in apolipoproteins and lipoproteins, enabling rapid and reliable determinations of levels of specific blood lipoprotein and/or apolipoprotein levels, including Apo B-100, Apo A-I, Apo A-II, Apo C-III, and Apo E, and thereby determination of relative ratios of HDL and LDL and LpaI and LpaII. In a preferred embodiment, the compositions are strips of a solid phase material coated with one or more of the antibodies and are referred to herein as "dipsticks". The dipsticks specifically bind a lipoprotein or apolipoprotein when dipped into a protein sample. The amount of lipid associated with a bound lipoprotein or the amount of apolipoprotein bound on the dipstick is quantitated using an appropriate method, for example, by staining with a lipid stain or reaction with a second labelled antibody. The intensity of the stain on the dipstick is proportional to the concentration of the lipoprotein lipid or apolipoprotein circulating in the blood and can be quantitated by comparison with standards containing known amounts of lipid. The dipsticks can be provided alone or in kits which enable the lay person to carry out the assay without the need of a physician or technical laboratory.

The MAbs can be used not only as components of dipsticks, but also in a variety of other methods, including enzyme immunoassays, radioimmunoassays as well as fluorescent and chemiluminescent immunoassays to determine lipoproteins and apolipoproteins in biological samples, and in purification of the apolipoprotein or lipoprotein with which they are immunoreactive.

DETAILED DESCRIPTION OF THE INVENTION

Methods and compositions to determine the concentration of specific lipoproteins and/or apolipoproteins, such as LDL and HDL, which when present at elevated levels in the body are causally related to an increased or decreased risk of CHD have been developed. In the preferred embodiment, blood lipoprotein and/or apolipoprotein molecules in a patient sample are bound to specific antibodies immobilized on specially prepared strips of solid phase material and to the bound lipoprotein and/or apolipoproteins visualized using specific colored staining reagents. The intensity of the color is proportional to the concentration of the lipid component or apolipoprotein component of the lipoprotein circulating in the blood.

I. Antibodies to Lipoproteins and Apolipoproteins

A. MAb methodology

Monoclonal antibody technology can be used to obtain MAbs useful in methods to rapidly and reliably determine blood lipoproteins and apolipoproteins (Galfré, G. and Milstein, C., *Methods Enzymol.*, 73:3–46 (1981) incorporated herein by reference). Briefly, hybridomas are produced using spleen cells from mice immunized with a particular apolipoprotein. The spleen cells of each immunized mouse is fused with mouse myeloma Sp 2/0 cells, for example using the polyethylene glycol fusion method of Galfré, G. and Milstein, C., *Methods Enzymol.*, 73:3–46 (1981). Growth of hybridomas, selection in HAT medium, cloning and screening of clones against antigens are carried out using standard methodology (Galfré, G. and Milstein, C., *Methods Enzymol.*, 73:3–46 (1981)).

HAT-selected clones are injected into mice to produce large quantities of MAb in ascites as described by Galfré, G. and Milstein, C., *Methods Enzymol.*, 73:3–46 (1981), which can be purified using protein A column chromatography (BioRad, Hercules, Calif.). MAbs are selected on the basis of their (a) specificity for a particular apolipoprotein, (b) high binding affinity, (c) isotype, and (d) stability.

B. Testing for specificity and affinity

MAbs can be screened or tested for specificity using any of a variety of standard techniques, including Western Blotting (Koren, E. et al., *Biochim. Biophys. Acta* 876:91–100 (1986)) and enzyme-linked immunosorbent assay (ELISA) (Koren, E. et al., *Biochim. Biophys. Acta* 876:91–100 (1986)), as described in more detail in the following examples.

In ELISA, separate wells in microtiter plates are coated with purified apolipoproteins which adsorb to the wall of the wells. The wells are then treated with a blocking agent, such as bovine serum albumin or nonfat milk proteins, to cover areas in the wells not bound by antigen. Ascites fluid or other antibody-containing preparation can then be applied to each well in varying concentrations and adequate time allowed for MAb to bind the antigen adsorbed on the wall of each well. The presence of MAb bound to antigen in a well can then be detected using a standard enzyme-conjugated anti-mouse antibody which will bind MAb that has bound to apolipoprotein in the well. Wells in which MAb is bound to antigen are then identified by adding a chromogenic substrate for the enzyme conjugated to the anti-mouse antibody and color production detected by an optical device such as an ELISA plate reader.

MAbs that bind to a single apolipoprotein with no significant detectable crossreactivity with other apolipoproteins are considered specific. To determine specificity of MAbs for a particular lipoprotein, individual wells on ELISA plates are coated with purified chylomicrons VLDL, LDL and HDL and subjected to the identical procedure. To determine whether or not two MAbs specific for the same apolipoprotein bind to different epitopes, a competitive ELISA is performed. For example, one of the MAbs is biotinylated. Mixtures containing a constant concentration of the biotinylated MAb and increasing concentrations of the nonbiotinylated MAb are incubated with wells coated with the apolipoprotein or lipoprotein antigen. Quantity of biotinylated antibody bound to the coated antigen is determined using a streptavidin-peroxidase conjugate and a chromogenic substrate. Decreased binding of the biotinylated MAb with increasing concentrations of the nonbiotinylated MAb indicates that the two MAbs compete for the same epitope. If the biotinylated MAb binds equally to the antigen as does the unlabelled MAb despite increasing concentrations of the nonbiotinylated MAb, the two antibodies do not compete for the same epitope. This competition can be complete or partial. Affinity of MAbs can be determined using radioactively labelled ($^{125}$I) lipoproteins or apolipoproteins and purified MAbs as described by Koren, E. et al., *Biochim. Biophys., Acta* 876:91–100 (1986), incorporated herein by reference).

C. Proteolytic cleavage of antibodies

It may be desirable to produce and use functional fragments of an MAb for a particular application. The well-known basic structure of a typical IgG molecule is a symmetrical tetrameric Y-shaped molecule of approximately 150,000 to 200,000 daltons consisting of two identical light polypeptide chains (containing about 220 amino acids) and two identical heavy polypeptide chains (containing about 440 amino acids). Heavy chains are linked to one another through at least one disulfide bond. Each light chain is linked to a contiguous heavy chain by a disulfide linkage. An antigen-binding site or domain is located in each arm of the Y-shaped antibody molecule and is formed between the amino terminal regions of each pair of disulfide linked light and heavy chains. These amino terminal regions of the light and heavy chains consist of approximately their first 110 amino terminal amino acids and are known as the variable regions of the light and heavy chains. In addition, within the variable regions of the light and heavy chains there are hypervariable regions which contain stretches of amino acid sequences, known as complementarity determining regions (CDRs). CDRs are responsible for the antibody's specificity for one particular site on an antigen molecule called an epitope. Thus, the typical IgG molecule is divalent in that it can bind two antigen molecules because each antigen-binding site is able to bind the specific epitope of each antigen molecule. The carboxy terminal regions of light and heavy chains are similar or identical to those of other antibody molecules and are called constant regions. The amino acid sequence of the constant region of the heavy chains of a particular antibody defines what class of antibody it is, for example, IgG, IgD, IgE, IgA or IgM. Some classes of antibodies contain two or more identical antibodies associated with each other in multivalent antigen-binding arrangements.

Proteolytic cleavage of a typical IgG molecule with papain is known to produce two separate antigen binding fragments called Fab fragments which contain an intact light chain linked to an amino terminal portion of the contiguous heavy chain via by disulfide linkage. The remaining portion of the papain-digested immunoglobin molecule is known as the Fc fragment and consists of the carboxy terminal portions of the antibody left intact and linked together via disulfide bonds. If an antibody is digested with pepsin, a fragment known as an F(ab')$_2$ fragment is produced which lacks the Fc region but contains both antigen-binding domains held together by disulfide bonds between contiguous light and heavy chains (as Fab fragments) and also disulfide linkages between the remaining portions of the contiguous heavy chains (*Handbook of Experimental Immunology. Vol* 1: *Immunochemistry,* Weir, D. M., Editor, Blackwell Scientific Publications, Oxford (1986)).

Fab and F(ab')$_2$ fragments of MAbs that bind particular blood apolipoproteins or lipoproteins can be used in place of whole MAbs in methods for detecting or quantifying such blood proteins or the lipids associated with such proteins. Because Fab and F(ab')$_2$ fragments are smaller than intact antibody molecules, more antigen-binding domains can be immobilized per unit area of a solid support than when whole antibody molecules are used. As explained below, rapid, easy and reliable assay systems can be made in which antibodies or antibody fragment that specifically bind apolipoproteins and lipoproteins are immobilized on solid phase materials.

D. Recombinant antibodies

Recombinant DNA methods have been developed which permit the production and selection of recombinant antibodies which are single chain antigen-binding polypeptides known as single chain Fv fragments (ScFvs or ScFv antibodies). ScFvs bind a specific epitope of interest and can be produced using any of a variety of recombinant bacterial phage-based methods, for example as described in Lowman, H. B. et al., *Biochemistry,* 30: 10832–10838 (1991); Clackson, T. et al., *Nature,* 352: 624–628 (1991); and Cwirla, S. E. et al., *Proc. Natl. Acad. Sci. USA,* 87: 6378–6382 (1990), incorporated herein by reference. These methods are usually based on producing genetically altered filamentous phage, such as recombinant M13 or fd phages, which display on the surface of the phage particle a recombinant fusion protein containing the antigen-binding ScFv antibody as the amino terminal region of the fusion protein and the minor phage coat protein g3p as the carboxy terminal region of the fusion protein. Such recombinant phages can be readily grown and isolated using well-known phage methods. Furthermore, the intact phage particles can usually be screened directly for the presence (display) of an antigen-binding ScFv on their surface without the necessity of isolating the ScFv away from the phage particle.

To produce an ScFv, standard reverse transcriptase protocols are used to first produce cDNA from mRNA isolated from a hybridoma that produces an MAb for an antigen of interest. The cDNA molecules encoding the variable regions of the heavy and light chains of the MAb can then be amplified by standard polymerase chain reaction (PCR) methodology using a set of primers for mouse immunoglobulin heavy and light variable regions (Clackson, T. et al., *Nature,* 352:624–628 (1991), incorporated herein by reference). The amplified cDNAs encoding MAb heavy and light chain variable regions are then linked together with a linker oligonucleotide in order to generate a recombinant ScFv DNA molecule. The ScFv DNA is ligated into a filamentous phage plasmid designed to fuse the amplified cDNA sequences into the 5' region of the phage gene encoding the minor coat protein called g3p. *Escherichia coli* bacterial cells are than transformed with the recombinant phage plasmids, and filamentous phage grown and harvested. The desired recombinant phages display antigen-binding domains fused to the amino terminal region of the minor coat protein. Such "display phages" can then be passed over immobilized antigen, for example, using the method known as "panning", see Parmley, S. F. and Smith, G. P., *Adv. Exp. Med. Biol.,* 251:215–218 (1989); Cwirla, S. E. et al., *Proc. Natl. Acad. Sci. USA,* 87: 6378–6382 (1990), incorporated herein by reference, to adsorb those phage particles containing ScFv antibody proteins that are capable of binding antigen. The antigen-binding phage particles can then be amplified by standard phage infection methods, and the amplified recombinant phage population again selected for antigen-binding ability. Such successive rounds of selection for antigen-binding ability, followed by amplification, select for enhanced antigen-binding ability in the ScFvs displayed on recombinant phages. Selection for increased antigen-binding ability may be made by adjusting the conditions under which binding takes place to require a tighter binding activity. Another method to select for enhanced antigen-binding activity is to alter nucleotide sequences within the cDNA encoding the binding domain of the ScFv and subject recombinant phage populations to successive rounds of selection for antigen-binding activity and amplification (see, Lowman, H. B. et al., *Biochemistry,* 30: 10832–10838 (1991) and Cwirla, S. E. et al., *Proc. Natl. Acad. Sci. USA,* 87: 6378–6382 (1990)).

Once an ScFv is selected, the recombinant antibody can be produced in a free form using an appropriate vector in conjunction with *E. coli* strain HB2151. These bacteria actually secrete ScFv in a soluble form, free of phage components (Hoogenboom H. R. et al., *Nucl. Acids Res.,* 19:4133–4137 (1991), incorporated herein by reference). The purification of soluble ScFv from the HB2151 bacteria culture medium can be accomplished by affinity chromatography using antigen molecules immobilized on a solid support such as AFFIGELTM (BioRad, Hercules, Calif.).

More recent developments in the recombinant antibody technology demonstrate possibilities for further improvements such as increased avidity of binding by polymerization of ScFvs into dimers and tetramers (Holliger, P. et al., *Proc. Natl. Acad. Sci. USA,* 90: 6444–6448 (1993); Mezes, P. *Construction and Biodistribution Studies of Multivalent Single-Chain Antibodies, The Fourth Annual IBC International Conference on Antibody Engineering,* December 1993, Coronado, Calif.; Ito, W. and Kurosawa, Y., J. Biol. Chem., 268: 20668–20675 (1993), incorporated herein by reference).

Because ScFvs are even smaller molecules than Fab or F(ab')$_2$ fragments, they can be used to attain even higher densities of antigen binding sites per unit of surface area when immobilized on a solid support material than possible using whole antibodies, F(ab')$_2$, or Fab fragments. Furthermore, recombinant antibody technology offers a more stable genetic source of antibodies, as compared with hybridomas. Recombinant antibodies can also be produced more quickly and economically using standard bacterial phage production methods.

As demonstrated below, the availability of hybridomas which produce MAbs to Apo B-100, Apo A-I, Apo A-II, Apo C-III, and Apo E enables the production of recombinant antibodies to these same antigens.

E. Anti-Apo Monoclonal antibodies (MAbs)

Unless specifically stated otherwise, the term "MAbs" includes natural and recombinant antibodies and fragments thereof.

MAbs to apolipoprotein (Apo) A-I, A-II, B, C-III and E can be used either alone or in various combinations to obtain a useful determination of the body's circulating levels of lipoproteins and/or apolipoproteins. MAbs used for making dipsticks, such as HB$_3$cB$_3$, D$_6$, AlbD$_5$, and CdB$_5$, described below, possess very high affinity constants ranging from $10^9$ to $10^{12}$ M$^{-1}$ as determined by the methods described by Koren, et al., *Biochim. Biophys. Acta,* 876:91–100 (1986); *Biochim. Biophys. Acta,* 876:101–107 (1986), incorporated herein by reference. An antibody coating a solid phase material is expected to bind a sufficient quantity of lipoprotein within a relatively short period of time (approximately two to five minutes), and to retain the captured lipoprotein during subsequent washing and staining for bound lipoprotein. It should be understood that while the descriptions below are the best antibodies presently known for making the compositions described herein, the methods described or incorporated by reference herein by citation to prior publications can be used by those skilled in the art to make other suitable antibodies having similar affinity and specificity which are functionally equivalent to those used in the following examples.

Monoclonal antibodies (MAbs) to apolipoproteins A-I, A-II, C-III and E were produced by immunization of Balb/c mice (Jackson Laboratories, St. Louis, Mo.) with purified apolipoproteins. All apolipoproteins were purified using well-established methods (curry, M. D. et al., *Clin. Chem.* 22:315–322 (1976); Curry, M. D. et al., *Clin. Chem.* 24:280–286 (1978); Curry, M. D. et al., *Biochim. Biophys. Acta* 439:413–425 (1976); and Curry, M. D. et al., *Biochim. Biophys. Acta* 617:503–513 (1980)).

From a library of several hundred MAbs, two antibodies directed against Apo A-I, one against Apo A-II, two against Apo B, one against Apo C-III and two against Apo E were selected for the methods and compositions described herein. The MAbs were selected on the basis of their (a) specificity, (b) high binding affinity, (c) isotype (class of antibody), and (d) stability under the conditions described below. Using commercially available isotype specific antimouse antibodies (Kirkegaard and Perry Laboratory, Gaithersburg, Md.) all of the MAbs were shown to belong to the IgG1 class and possess kappa light chains.

Antibodies to Apo B

Two MAbs specific for Apo B, D$_6$ and HB$_3$cB$_3$ MAbs, were developed and found to be useful for the methods and compositions described below. D$_6$ and HB$_3$cB$_3$ MAbs bind to sterically distant epitopes on Apo B.

Antibodies to Pan B

D$_6$ MAb is an antibody with equal binding and high affinity for all Apo B-containing lipoproteins in human plasma, as described by Koren, E. et al., *Biochim. Biophys. Acta,* 876:91–100 (1986); Koren, E. et al., *Biochim. Biophys. Acta,* 876:101–107 (1986), specifically including Apo B-48 and Apo B-100. D$_6$ binds to an epitope localized at the amino terminal half of Apo B and recognizes both B-48 and B-100.

D$_6$ was produced after immunization of mice with a narrow cut of low density (1.021 to 1.006 g/ml) lipoproteins (LDL) containing apolipoprotein B (Apo B) as a sole protein (Smith, L. C. et al., *Ann. Rev. Biochem.,* 47: 751–777 (1978)). Hybridomas were produced using spleen cells from immunized mice. The fusion of spleen cells with mouse myeloma Sp 2/0 cells was carried out using the polyethylene glycol method of Galfré, G. and Milstein C., *Methods Enzymol.,* 73: 3–46 (1981). Growth of hybridomas, selection in HAT medium, cloning and screening of hydridoma clones against specific antigens were carried out using standard methodology (Galfré, G. and Milstein C., *Methods Enzymol.,* 73: 3–46 (1981), incorporated herein by reference). Selected clones were injected into mice to produce large quantities of antibodies in ascites (Galfré, G. and Milstein C., *Methods Enzymol.,* 73: 3–46 (1981)) followed by purification of MAbs using protein A column chromatography (Bio-Rad, Hercules, Calif.).

Antibodies to Apo B-100

Conventional ways of producing MAbs to Apo B-100 include immunization of mice with LDL. This approach is convenient because it is relatively simple to isolate LDL. However, MAbs produced using LDL as an immunogen tend to be sensitive to conformational changes of Apo B-100 caused by variations in the lipid composition of LDL particles. For example, Apo B-100 epitopes are less reactive with a number of anti-Apo B MAbs due to the presence of various amounts of triglycerides (Keidar, S. et al., *Metabolism,* 39: 281–288 (1990); Galeano, N.F. et al., *J. Biol. Chem.,* 269:511–519 (1994); Harduin, P. et al., *Arterioscl. Thromb.,* 13: 529–535 (1993)).

For the methods and compositions described herein, an MAb is desired that fulfills two important criteria: (i) selective recognition of LDL and (ii) high and invariable reactivity with LDL particles, irrespective of possible variations in their lipid composition and/or conformation. Such an MAb must, therefore, recognize a stable, conformation-independent epitope which is uninfluenced by the lipid content and which is equally expressed in all LDL particles, but inaccessible in VLDL and chylomicrons. A MAb possessing these properties has not been previously described. For example, a detailed comparison of two known, potentially LDL specific MAbs demonstrated that neither of them can meet the above requirements (Milne, R. et al., *J. Biol. Chem.*, 264:19754–19760 (1989); WO 93/18067). Cross-reactivity with VLDL, especially in samples with high VLDL concentrations appears to be the major obstacle even in the case of most promising "anti-LDL" MAbs such as 8A2.1 and 4B5.6 (WO93/18067) (La Belle, M. et al., *Clin. Chim. Acta*, 191:153–160 (1990)). To obtain an anti-LDL MAb whose binding to LDL particles is not dependent on variations in LDL composition and/or conformation, mice were immunized with soluble Apo B-100 which had been delipidized, reduced, carboxymethylated and, purified by electrophoration in polyacrylamide gels containing 8 M urea (Lee, D. M. et al., *Biochim. Biophys. Acta*, 666: 133–146 (1981)). Immunization with such delipidized, soluble, reduced, carboxymethylated, and electrophoretically purified Apo B-100 has not been previously reported.

The spleen cells of mice that were immunized using the soluble and electrophoretically purified Apo B, were then used to produce hybridomas according to standard hybridoma methods. A resulting MAb, $HB_3cB_3$, binds selectively to LDL particles produced by a hybridoma generated using spleen cells immunized with the soluble and electrophoretically purified Apo B.

$HB_3cB_3$ binds to the epitope near the T2 carboxy terminal region of B-100, exclusively, and does not recognize B-48. The epitope recognized by $HB_3cB_3$ may be conformationally changed or masked by lipids and/or other apolipoproteins present in VLDL. Chylomicrons are not recognized by $HB_3cB_3$ because they lack Apo B-100. The $HB_3cB_3$ MAb, and LDL-binding fragments derived therefrom, can be used as an LDL-specific binding molecule in all of the compositions and methods described herein because of its specificity for LDL and lack of cross-reactivity with other lipoproteins.

Antibodies to Apo A-I

Two MAbs raised against apolipoprotein A-I were selected from a library of MAbs for developing rapid and sensitive means and methods of detecting lipoproteins predictive of risk of CHD. Both of them bind to HDL with a high affinity and show negligible reactivity with any other lipoprotein density class. The two anti-Apo A-I MAbs, $AIbD_5$ and $AIbE_2$, bind to sterically distant epitopes since they do not compete with each other in their binding to either delipidized and purified Apo A-I or intact HDL particles. Both MAbs to Apo A-I bind with high affinity to delipidized Apo A-I and to HDL and show negligible or no binding to LDL, VLDL, chylomicrons and Apos A-II, C-III and E as shown in Tables 1 and 2 below.

Antibodies to Apo A-II

An MAb to Apo A-II was produced using purified Apo A-II as an immunogen. This antibody binds with high affinity to HDL and is capable of removing all the HDL particles containing Apo A-II (LP-A-I:A-II particles) from plasma or serum, leaving the HDL particles without Apo A-II (LP-A-I particles) intact. This anti-Apo A-II MAb, $CdB_5$, is described by Koren, E. et al., *Arteriosclerosis*, 6:521a (1986); Alaupovic, P. et al., *J. Lipid Res.*, 32:9–19 (1991).

Antibodies to Apo C-III

An MAb to Apo C-III, $XbA_3$, which is useful in quantification of VLDL particles is described by Koren, E. et al., *Atherosclerosis*, 95:157–170 (1992).

Antibodies to Apo E

Two MAbs to Apo E are described by Koren, E. et al., *Atherosclerosis*, 95:157–170 (1992). One of them, $EfB_1$, binds preferably to Apo E associated with VLDL which are precipitated by heparin whereas the other ($EfD_3$) binds predominantly to Apo E in HDL which are not precipitated by heparin treatment of a sample.

II. MAbs Immobilized on Solid Phase Materials

A. Dipsticks

Antibodies can be bound to a solid phase material for use in assays or purification procedures described herein. Various types of adsorptive materials, such as nitrocellulose, Immobilon™, polyvinyldiene difluoride (all from BioRad, Hercules, Calif.) can be used as a solid phase material to bind the anti-lipoprotein antibodies. Other solid phase materials, including resins and well-plates or other materials made of polystyrene, polypropylene or other synthetic polymeric materials can also be used. In the preferred embodiment for assaying lipoprotein concentrations, pieces or strips of these materials are coated with one or more antibodies, or functional fragments thereof, directed against specific epitopes of HDL, LDL, other lipoproteins, or apolipoproteins for use in patient samples. Such strips are referred to herein as "dipsticks". The dipsticks may also be attached to one end of a longer strip of a solid support material, such as plastic, which can serve as a handle for dipping a dipstick into a solution or sample, such as a sample of whole blood, blood plasma, or blood serum. The plastic handle can also serve as a tether so that multiple dipsticks can be attached to a common support. Such a multi-strip design may be particularly useful in a set-up for testing multiple lipoproteins and/or apolipoproteins simultaneously.

Although various sizes of dipsticks are possible, typically, pieces of the solid phase material that are coated with antibody have the general dimensions of 0.5 cm×0.5 cm and can be attached to the longer solid support strips having general dimensions of 0.5 cm×5 cm. Such dimensions permit an accurate determination of lipoprotein or apolipoprotein levels in as little as 100 μl of blood.

The dipsticks described herein contain one or more regions containing immobilized antibodies specific for particular epitopes on apolipoproteins or lipoproteins.

B. Coating solid phase material with antibodies

Adsorption

The strips of solid phase material, as used to make dipsticks, may be coated with antibodies by any of a variety of methods. If the strips are made of a protein-receptive solid phase material that adsorbs antibodies, such as nitrocellulose or polyvinyldiene difluoride (PVDF) membrane, the material can be coated directly with antibody by immersing the solid phase material directly into a solution of antibody. However, a random interaction between the antibody molecules and the solid phase material can occur with this method and a certain percentage (up to 30 percent) of the antibody molecules that adsorb to the strips are immobilized in an orientation that makes their antigen-binding sites unavailable to bind their cognate lipoprotein or apolipoprotein antigen molecules.

Avidin-Biotin Complexes

The proportion of antibody molecules on the dipsticks which are correctly oriented to bind their cognate antigens can be substantially increased if antibody molecules are attached to the solid phase material using avidin-biotin complexes. The strips of solid phase material are first coated with avidin or streptavidin (both available commercially, for example, from Sigma Chemical Co., St. Louis, Mo.). PVDF strips can be coated with avidin by incubating the strips in a solution of avidin (10 mg avidin in 3.5 ml of phosphate buffered saline, PBS) for 48 hours at 4° C. The avidin-coated strips are then incubated with antibody molecules which were previously biotinylated in their Fc domains (for example, using a biotin-LC-hydrazide labelling kit, Pierce, Rockford, Ill.). The avidin molecules adsorbed on the solid phase material specifically bind the biotin linked to the Fc domains of the antibodies. In this way, the antibodies become attached to the solid phase material, optimally oriented with their carboxy terminal Fc regions linked to the surface of the dipstick (via numerous biotin-avidin complexes) and with their antigen-binding domains directed away from the surface of the dipsticks and available for binding their cognate lipoprotein or apolipoprotein antigens in solution. Alternatively, the same linkage can be achieved by chemically coupling biotin to the solid phase material and covalently attaching avidin to the Fc portion of the antibody molecules.

Use of the avidin (or streptavidin)-biotin system to coat strips with antibody yields dipsticks with a significantly higher capacity for binding lipoproteins and/or apolipoproteins than dipsticks which was made by simply applying antibody directly to the strips of solid phase material. The higher binding capacity of the dipsticks containing antibodies adsorbed to the solid phase using the avidin-biotin conjugation system results in a more sensitive dipstick. This is of a particular importance when dipsticks pre-stained with lipid or protein stains are used to capture lipoproteins, as described below.

After antibody has been adsorbed directly on the protein receptive dipstick material, or indirectly through avidin (or streptavidin), the strips are treated ("blocked") with a blocking agent in order to minimize nonspecific adsorption of lipoproteins, lipids, or apolipoproteins to unoccupied sites on the dipstick material. The dipsticks are treated with any of a variety of blocking agents such as bovine serum albumin (BSA), gelatin, Tris™, all of which are available commercially (Sigma, St Louis, Mo.) or nonfat milk proteins. For example, avidin-coated PVDF strips can be blocked with 2 percent (w/v) milk blocking solution (Kirkegaard and Perry Laboratories, Gaithersburg, Md.) for 48 hours at 4° C.

Antibodies can also be chemically coupled to the substrate to form the dipsticks.

C. Design of dipsticks

A dipstick may contain more than one antibody so that the single dipstick can be used to detect more than one apolipoprotein or lipoprotein. For example, two or more separate pieces of a solid phase material, each coated with an antibody directed against a particular apolipoprotein or lipoprotein, can be attached to a longer strip of solid support to produce a dipstick with two or more separate areas, each specific for a particular lipoprotein or apolipoprotein. The means to attach the solid phase material to a solid support should not impair the function of the molecules coated on the solid phase material and must be secure enough to withstand soaking in whole blood, serum, plasma, and the other solutions described herein which are used to wash, stain, and preserve the dipsticks. A preferred method of attaching antibody-coated solid phase material to a longer strip of solid support is to use a glue or cement such an acrylate adhesive (for example, SUPER GLUE™, Super Glue Corporation, Hollis, N.Y.; DURO™, Loctite Corporation, Cleveland, Ohio).

Dipsticks can be designed for quantification of one or more lipoproteins or apolipoproteins in a blood sample. In one embodiment, dipsticks designed for quantification of a lipoprotein or apolipoprotein contain a single antigen-binding area which is dipped into a blood sample, stained for bound lipid lipoproteins or apolipoprotein, and visually compared with a set of printed colored standards to determine the concentration of the particular lipoprotein or apolipoprotein.

In addition, dipsticks can be designed for detecting a change in the relative level of particular lipoproteins or apolipoproteins in a blood sample. Dipsticks can be designed for detecting a change in the relative level of specific lipoproteins or apolipoproteins which contain two antigen-binding areas, each area coated with a different antibody. After processing the dipstick to detect the lipoprotein or apolipoprotein antigens bound by each antibody, the relative intensities of the colors in the two areas of the dipstick are compared as an indication of the relative concentrations of the two antigens in the blood.

A determination of relative levels of specific lipoproteins or apolipoproteins can also be made by simultaneously using two separate dipsticks. However, a single dipstick with two antigen binding areas is generally easier to use, especially for the lay person, and an assessment of relative color intensities in two areas in close proximity on a single dipstick is relatively easy to make even for the untrained observer.

A simple comparison of relative color intensities in two areas may be sufficient for an assessment of an increase or decrease in a lipoprotein or apolipoprotein ratio. However, in a preferred embodiment, each doublet of stained areas is also compared with printed colored standards covering an appropriate range of ratios of color intensities.

In another embodiment, dipsticks are made that contain distinct areas or spots of known amounts of molecules whose levels are to be determined by the dipstick. For example, known amounts of lipid, lipoproteins and/or apolipoproteins are placed on the dipsticks using methods such as those used for attaching antibodies to the solid phase material described above. Such known amounts of lipids, lipoproteins, and apolipoproteins present on dipsticks act as "internal standards", whose staining intensity can be compared to that in the antigen-binding areas of the dipstick in order to estimate the amount of antigen bound by the antibodies on the dipstick.

D. Storage of dipsticks

Although there is a possibility that some antibodies could be adsorbed onto a solid phase material, dried, and subsequently rehydrated without significant loss of their binding capacity, most of the antibodies on dipsticks are better preserved if stored in at least a small amount of aqueous buffer, such as phosphate buffered saline (pH 7.4), in order to retain their binding capabilities. For example, the dipsticks can be stored damp in sealed foil or plastic bags containing enough buffer to prevent dehydration. The buffer may also contain an appropriate quantity (25 to 50 percent) of a stabilizing agent such as glycerol or sucrose. The dipsticks in the sealed bags can be stored in such buffers at temperatures ranging generally from 4 to 25° C., for up to three months without significant loss of accuracy. The dipsticks should be removed from the storage bag immediately prior to use, and rinsed for 30 seconds under tap water or physiological buffer (for example, PBS) (at a temperature less than 40° C. to avoid denaturation of the immobilized MAb) in order to remove residual stabilizing agents and storage buffer.

III. Determination of Lipoprotein Concentrations

The crucial reagents in this approach are the antibodies or functional fragments of the antibodies, which specifically recognize and bind a particular lipoprotein, leaving other lipoproteins in the sample unadsorbed. In order to assay a sample of whole blood, serum or plasma for HDL or LDL, dipsticks are incubated with EDTA-treated or heparinized blood for 2 to 5 minutes at room temperature. After incubation, each strip is washed to remove unbound blood, (for example, under tap water for 0.5 to 1 minute at temperatures not exceeding 40° C. The dipsticks are then stained, for example, by immersing the dipsticks in a solution of stain such as Sudan Red 7B for 2 to 5 minutes at room temperature to stain the lipid present in the bound lipoprotein particles. Excess stain is then removed by an additional wash. Residual moisture or stain may be drawn off by touching an absorbent towel with the edge of dipstick. The "face" of the dipstick, that is, the side of the dipstick containing immobilized antibody, should not be blotted, which might disturb the immobilized antibody and/or bound antigen. After drying, the intensity of the staining can be compared with standardized colored strips to determine the concentration of lipoprotein in the blood.

A number of other lipid stains such as Oil Red O or Sudan Black B can be also used for staining of dipsticks. However, in the preferred embodiment, Sudan Red 7B, also known as Fat Red 7B (Sigma, St. Louis, Mo.), dissolved in a mixture of methanol and NaOH is used because of its high color intensity. In another embodiment lipoproteins are stained prior to being bound to antibody ("pre-stained"), such as antibody on a dipstick, using any of the above mentioned lipid stains dissolved in propylene glycol (Wollenweber, J. and Kahlke, W., *Clin. Chim. Acta,* 29:411–420 (1970)). The pre-stained blood, plasma or serum sample is then incubated, for example, with anti-LDL or anti-HDL dipsticks. After washing and drying, the quantity of pre-stained lipoprotein captured by the dipstick is determined visually according to the intensity of the color, for example, by comparison with a set of printed colored standards.

IV. Determination of Apolipoprotein Concentrations

Sandwich Assays

The methods described above for the detection of lipoproteins depend on the staining of lipids associated with the lipoproteins which have been bound by a lipoprotein-specific antibody on the dipstick. The determination of the concentration of a specific apolipoprotein in blood samples requires a "sandwich" method of detection in which at least two anti-apolipoprotein antibodies with distinct specificities for two different epitopes of the same apolipoprotein are used. In a preferred embodiment, two MAbs are used that bind to separate epitopes of the apolipoprotein. One of the two MAbs is conjugated to an enzyme, for example, horseradish peroxidase, alkaline phosphatase, or to biotin which in turn binds to an avidin- or streptavidin-enzyme conjugate of an enzyme-based chromogenic labeling system. The enzyme-conjugated anti-apolipoprotein MAb is added to and mixed with the blood, serum or plasma sample. The second MAb is immobilized on a dipstick. During the incubation with the blood sample, typically 10 minutes at room temperature), the enzyme-conjugated MAb binds to its cognate epitope and forms soluble antibody-antigen complex. The dipstick is then immersed into the blood sample and incubated for 2 to 5 minutes at room temperature to allow the immobilized MAb to bind the other epitope of the same apolipoprotein. The dipstick is then removed and washed as described above. After washing, the strip is immersed into a solution containing the appropriate chromogenic substrate (2 to 5 minutes at room temperature) for the enzyme that was conjugated to the first MAb for example, 3,3', 5,5'-tetramethylbenzidine ("TMB") or 4-chloro-1-naphthol for horseradish peroxidase; or 5-bromo-4-chloro-3-indolyl phosphate for alkaline phosphatase. The dipstick is washed, dried, and the color developed and compared with color standards which correspond to various concentrations of apolipoprotein in the blood sample.

Alternatively, the dipstick can first be incubated with a blood sample for 2 to 5 minutes to bind the apolipoprotein and then washed and immersed into the solution of the MAb-enzyme complex for 10 minutes at room temperature. After an additional washing, the dipstick is immersed into a solution of chromogenic substrate and stained as explained above.

For example, in a noncompetitive "sandwich" version of ELISA, anti-LDL MAb is adsorbed to the wells of a microtiter plate. A plasma or serum sample is added to wells of a microtiter plate coated with anti-LDL MAbs. The sample is incubated in the wells to allow the anti-LDL MAb to bind LDL in the plasma or serum sample. The unbound components of the sample are then removed and the quantity of LDL-Apo B captured by the $HB_3cB_3$ MAb is determined using a Pan B ($D_6$) MAb-peroxidase complex and chromogenic peroxidase substrate as described above. Peroxidase labeled polyclonal antibody to Apo B may be used instead of Pan B MAb.

In a competitive variation of ELISA, anti-LDL $HB_3cB_3$ MAb is mixed with a sample of plasma or serum and allowed to bind to LDL. This mixture is then added to the ELISA microtiter plate coated with LDL. MAb molecules that did not react with LDL in the sample are free to bind to the layer of LDL immobilized on the plate. The higher the concentration of LDL is in the plasma or serum sample, the less anti-LDL MAb will bind to LDL on the plate. The quantity of anti-LDL MAb bound to the plate is determined using any of the commercially available enzyme-conjugated secondary antibodies such as, alkaline phosphatase or peroxidase conjugated to goat anti-mouse IgG, (Kirkegaard and Perry Laboratories, Gaithersburg, Md.), and subsequent incubation with an appropriate chromogenic substrate. Alternatively, the anti-LDL MAb can be conjugated to an enzyme, for example to form an anti-LDL MAb-peroxidase or alkaline phosphatase complex, and thereby eliminate the use of an enzyme-conjugated secondary antibody, with the same results.

In an alternate embodiment of the sandwich method, only one of the antibodies to the particular apolipoprotein is an MAb and the other antibody is a polyclonal anti-apolipoprotein antibody. This method can work as well as the two MAb sandwich method described above, if the one MAb is specific for the particular apolipoprotein of interest, that is, does not cross-react with other apolipoproteins. Either the MAb or the polyclonal antibody may be the immobilized or the enzyme-conjugated antibody in this embodiment of the sandwich method. This method is most accurate when the MAb (whether enzyme-conjugated or immobilized) is allowed to bind to the apolipoprotein antigen first, and the polyclonal anti-apolipoprotein is allowed to bind to the apolipoprotein second. This stepwise procedure prevents underestimation of the quantity of the particular apolipoprotein in the blood sample by insuring 1) that none of the polyclonal antibody molecules are given the first opportunity to bind, and thereby block, the specific epitope recognized by the MAb molecules and 2) that essentially only those apolipoprotein molecules recognized by the MAb are detected. The highly specific anti-Apo B MAb $HB_3cB_3$ described herein is thus an example of an MAb useful in any of the above-described sandwich methods as applied to the detection and quantification of Apo B.

The above described sandwich method, to determine the amount of apolipoprotein in a sample, is useful not only for quantification of single apolipoproteins, but also for analysis of ratios between various apolipoproteins and lipoproteins in which case dipsticks with two or more antigen binding areas are used as described above.

In another embodiment, any of the above described enzyme-conjugated monoclonal or polyclonal anti-apolipoprotein antibodies is replaced with a "stained" antibody, that is, an antibody coupled with a protein stain such as nitro blue tetrazolium (Glenner, G. G. Formazans and Tetrazolium Salts, In: H. J. Conn's Biological Stains, pp. 225–235. The Williams and Wilkins Company USA 1990; U.S. Pat. No. 4,786,589)). Such a "stained" or "colored" antibody is mixed with a blood, plasma or serum sample to bind, and thereby, pre-stain the antibody's cognate apolipoprotein or lipoprotein in the sample. An antibody coated dipstick is then immersed into the sample in order to absorb the lipoprotein which has been pre-stained via binding to the stained antibody. After washing and drying the quantity of pre-stained lipoprotein is determined visually by comparing the color of the dipstick with a set of printed color standards.

In addition, the above-described sandwich method can be used to detect any blood protein of interest in a particular sample, provided, as described above, that either two distinct MAbs are available which do not interfere with each other's binding to the particular protein, or one MAb and a polyclonal antibody are available for the particular protein and the MAb is allowed to bind to the particular protein before the polyclonal antibody.

Antibody-antigen precipitation techniques and enzyme-linked immunosorbent assays (ELISA)

Anti-LDL MAbs, such as $HB_3cB_3$ are useful for quantification of LDL-cholesterol in antibody-antigen precipitation techniques and enzyme-linked immunosorbent assays (ELISA). For example, in a precipitation method the anti-LDL MAb is added to human serum or plasma and allowed to bind to LDL. The immune complex of LDL bound to anti-LDL MAb is then precipitated by mixing in an excess amount of protein A or an anti-mouse IgG polyclonal antibody. Precipitation of the complexes is enhanced by centrifuging the mixture and the supernatant liquid is discarded. The precipitate containing LDL is then washed and dissolved in 8 M urea in PBS or treated with detergents such as Triton X-100 and cholic acid (Sigma, St. Louis, Mo.). This is followed by determination of LDL-cholesterol using an enzymatic assay for cholesterol (Sigma, St. Louis, MO).

Fluorescent immunoassay

Antibodies specific for LDL can be also used in fluorescent immunoassay. A number of fluorescent compounds such as fluorescein isothiocyanate, europium, lucifer yellow, rhodamine B isothiocyanate (Wood, P. In: *Principles and Practice of Immunoassay,* Stockton Press, New York, pages 365–392 (1991), incorporated herein by reference) can be used to label anti-LDL MAb or LDL. In conjunction with the known techniques for separation of antibody-antigen complexes, these fluorophores can be used to quantify LDL. The same applies to chemiluminescent immunoassay in which case either anti-LDL MAb or LDL can be labeled with isoluminol or acridinium esters (Krodel, E. et al., In: *Bioluminescence and Chemiluminescence: Current Status.* John Wiley and Sons Inc. New York, pp 107–110 (1991); Weeks, I. et al., *Clin. Chem.* 29:1480–1483 (1983), incorporated herein by reference). Radioimmunoassay (Kashyap, M. L. et al., *J. Clin. Invest.* 60:171–180 (1977)) is another technique in which anti-LDL MAb can be used after coupling of anti-LDL MAb or LDL with a radioactive isotope such as $^{125}I$. Some of these immunoassays can be easily automated by the use of appropriate instruments such as the IMX™ (Abbott, Irving, Tex.) for a fluorescent immunoassay and Ciba Corning ACS 180™ (Ciba Corning, Medfield, Mass.) for a chemiluminescent immunoassay.

V. Purification of Apolipoprotein

Although described herein with reference to the use of the specific anti-apolipoprotein antibodies for diagnostic purposes, the antibodies can be immobilized to resins or well plates or other inert substrates for use in purification of the apolipoprotein which the antibody is immunoreactive with. Antibodies specific for LDL can also be used to make immunoaffinity columns in which anti-LDL MAb is conjugated to a solid support. In addition to use in LDL purification, such immunoaffinity columns can be used to selectively remove LDL from a patient's blood using an extracorporeal circulation device. In a preferred embodiment, the antibody is bound to an acrylamide or agarose resin particulate such as SEPHAROSE™ (Pharmacia Fine Chemicals, Piscataway, N.J.) or Affi-GEL™, (Bio-Rad, Hercules, Calif.), and placed in a chromatography column. The sample from which the apolipoprotein is to be purified is applied to the column, the material which is not bound by the antibody is washed from the column, and the bound lipoprotein is eluted from the antibody using a salt gradient or other standard technique.

The present invention will be further understood by reference to the following non-limiting examples.

EXAMPLE 1

Determination of Binding Specificity of Apolipoprotein MAbs

To determine the binding specificity of the anti-Apo A-I MAb AIbD5, ELISA plates were coated with antigens using concentrations indicated in the left column of Table 1, below. Each antigen was incubated with the $AIbD_5$, MAb (10 μg/ml) followed by washing and detection of the bound MAb with a goat anti-mouse-peroxidase conjugate. Each number represents an average optical density from three separate experiments. $AIbD_5$ MAb bound strongly to Apo A-I and HDL, but exhibited no significant binding to other antigens.

TABLE 1

Binding Specificity of AIbD5 MAb (anti-Apo A-I) to apolipoprotein and lipoproteins.

| Antigen (μg protein per ml) | Apolipoproteins | | | | Chylo- microns | Lipoproteins | | |
| --- | --- | --- | --- | --- | --- | --- | --- | --- |
| | A-I | A-II | C-III | E | | VLDL | LDL | HDL |
| 80 | 1.620 | 0.105 | 0.084 | 0.090 | 0.153 | 0.205 | 0.211 | 1.732 |
| 40 | 1.012 | 0.090 | 0.060 | 0.071 | 0.095 | 0.132 | 0.130 | 1.361 |
| 20 | 0.841 | 0.080 | 0.053 | 0.060 | 0.080 | 0.095 | 0.098 | 1.045 |
| 10 | 0.520 | 0.075 | 0.032 | 0.045 | 0.080 | 0.090 | 0.087 | 0.783 |
| 5 | 0.210 | 0.063 | 0.040 | 0.038 | 0.075 | 0.080 | 0.075 | 0.400 |
| 2.5 | 0.135 | 0.020 | 0.020 | 0.018 | 0.060 | 0.047 | 0.050 | 0.268 |

To determine the binding specificity of the Apo A-I MAb, $AIbE_2$, ELISA plates coated with antigen concentrations indicated in the left column of Table 2, below. As in the case of $AIbD_5$ MAb, each antigen was incubated with the $AIbE_2$ MAb (10 μg/ml) followed by washing and detection of the bound MAb with a goat anti-mouse-peroxidase-conjugate. The numbers represent average optical density readings from three separate experiments. $AIbE_2$ bound strongly to Apo A-I and HDL, but exhibited no significant binding to the other antigens.

The epitopes recognized by the MAbs $AIbD_5$ and $AIbE_2$ are different and sterically separated since these antibodies did not compete with each other when allowed to bind simultaneously to HDL.

TABLE 2

Binding to AIbE$_2$ MAb (anti-Apo A-I) to apolipoproteins and lipoproteins

| Antigen (µg protein per ml) | Apolipoproteins | | | | Chylo-microns | Lipoproteins | | |
|---|---|---|---|---|---|---|---|---|
| | A-I | A-II | C-III | E | | VLDL | LDL | HDL |
| 80 | 1.205 | 0.095 | 0.061 | 0.076 | 0.107 | 0.183 | 0.200 | 1.431 |
| 40 | 0.780 | 0.080 | 0.060 | 0.053 | 0.103 | 0.115 | 0.163 | 1.108 |
| 20 | 0.337 | 0.083 | 0.065 | 0.060 | 0.098 | 0.108 | 0.108 | 0.860 |
| 10 | 0.340 | 0.071 | 0.047 | 0.059 | 0.080 | 0.083 | 0.099 | 0.495 |
| 5 | 0.189 | 0.070 | 0.053 | 0.045 | 0.063 | 0.070 | 0.063 | 0.231 |
| 2.5 | 0.105 | 0.068 | 0.048 | 0.040 | 0.060 | 0.058 | 0.060 | 0.150 |

EXAMPLE 2

Production of Anti-Apo B-100 Antibody, HB$_{3c}$B$_3$

The MAb to Apo B, HB$_3$cB$_3$, was produced by immunizing mice with Apo B-100 molecules which had been delipidized, reduced, carboxymethylated, and purified by electrophoresis on a polyacrylamide gel containing 8 M urea. Delipidized Apo B-100 readily precipitates due to self-aggregation in aqueous media. In addition to the self-aggregation, Apo B-100 is also susceptible to fragmentation during the solubilization procedure (Socorro, L. and Camejo, G.J. *Lipid Res.,* 20:631–645 (1979); Olofsson, S. O. et al., *Biochemistry,* 19:1059–1064 (1980)). Therefore, in order to separate self-aggregated and degraded material from the preserved protein, the delipidized, reduced, and carboxymethylated Apo B-l00 was electrophoresed on a polyacrylamide gel containing 8 M urea. Coomassie blue staining of the urea-polyacrylamide gel revealed three distinct bands. The most prominently stained band in the urea-containing polyacrylamide gel was cut out immediately after the completion of electrophoresis and subcutaneously injected (while still in the gel) into mice without further manipulation of addition or adjuvants. The most prominently stained band on the urea-polyacrylamide gel had previously been shown to be pure Apo B-100, as confirmed by eluting the band from the urea-containing gel and electrophoresing it under reducing and denaturing conditions on a standard SDS-containing polyacrylamide gel. The SDS-gel revealed a single protein band of the expected mobility of Apo B-100.

Approximately 10 to 20 µg of the Apo B-100 band excised from the urea-containing gel was injected four times at various locations over a period of two months. The mice immunized with the Apo B-100 according to this procedure were then used in standard methods to produce hybridomas. Out of forty-two hybridomas which produced MAbs that bound Apo-B-100, only one, HB$_3$cB$_3$, produced a MAb that bound exclusively to LDL, as shown in Table 3, below.

To characterize the binding specificity of the HB$_3$cB$_3$ MAb, ELISA plates were coated with lipoproteins using concentrations indicated in the left column of Table 3 below. Each antigen was incubated with the HB$_3$cB$_3$ MAb (10 µg/ml) followed by washing and detection of the bound MAb with a goat anti-mouse IgG-peroxidase conjugate. Each number represents an average optical density reading from three separate experiments. HB$_3$cB$_3$ MAb showed a strong and exclusive binding to LDL. Identical results were obtained with competitive ELISA (see below) in which the binding of HB$_3$cB$_3$ MAb to LDL absorbed to the wells of an ELISA plate was found to be inhibited only by LDL.

TABLE 3

Binding Specificity of HB$_3$cB$_3$ MAb (anti-Apo B-100) to Lipoproteins

| Antigen (µg protein per ml) | Lipoproteins | | | |
|---|---|---|---|---|
| | Chylo-microns | VLDL | LDL | HDL |
| 80 | 0.085 | 0.098 | 1.900 | 0.078 |
| 40 | 0.081 | 0.095 | 1.432 | 0.080 |
| 20 | 0.072 | 0.084 | 1.003 | 0.082 |
| 10 | 0.060 | 0.068 | 0.605 | 0.075 |
| 5 | 0.043 | 0.063 | 0.211 | 0.060 |
| 2.5 | 0.040 | 0.051 | 0.140 | 0.060 |

HB3cB$_3$ MAb binds to Apo B-100 in Western blots and shows no significant reactivity with any other plasma apolipoproteins or proteins. Western blotting also reveals that HB$_3$CB$_3$ MAb binds to the so-called T$_2$ fragment of Apo B-100 which represents a carboxy terminal 1,287 amino acid piece of Apo B-100 (Cardin, A. D. et al. *J. Biol. Chem.,* 259: 8522–8528 (1984)). The HB$_3$cB$_3$ MAb recognizes an epitope outside of the receptor binding domain localized at the amino terminus of the T$_2$ fragment because it does not interfere with the binding of LDL to the LDL receptor on cultured human skin fibroblasts and human hepatoma HepG2 cells.

HB$_3$cB$_3$ MAb binds strongly and specifically to LDL with little or no significant reactivity with VLDL (Table 3, above). Furthermore, immunoaffinity chromatography of human serum using HB$_3$cB$_3$ MAb immobilized on an AFFI-GEL™ column (Bio-Rad, Hercules, Calif.) always yields a lipoprotein fraction with typical β electrophoretic mobility, free of any other lipoproteins. Identical results were obtained with normal, hypertriglyceridemic as well as hypercholesterolemic sera as determined using a commercial lipoprotein electrophoresis kit (Ciba Corning, Medfield, Mass.). In addition, crossed immunoelectrophoresis (Koren, E., et al., *Biochemistry,* 21:5347–5351 (1982)), of the lipoproteins retained by the HB$_3$cB$_3$ column revealed only one symmetrical Apo B peak very similar in shape and mobility to ultracentrifugally isolated LDL. These immunoaffinity chromatography results confirmed the specificity of HB$_3$cB$_3$ MAb for LDL as well as the lack of reactivity with VLDL.

Further evidence for the LDL specificity of HB$_3$cB$_3$ MAb came from a comparison between the LDL-Apo B concentrations as determined in human sera using an ELISA with HB$_3$cB$_3$ MAb and the concentrations of LDL-cholesterol determined using a commercially available LDL-cholesterol assay kit (Sigma, St. Louis, Mo.). In the competitive ELISA method, the wells of microtiter plates were coated with LDL and blocked with 0.1% nonfat milk proteins (Kirkegaard Perry Laboratories, Gaithersburg, Md.). This was followed by incubating dilutions of human sera with HB$_3$cB$_3$ MAb for 18 hours at 4° C. These mixtures were then pipetted into wells coated with LDL and incubated for 3 hours at room temperature. During this time, HB$_3$cB$_3$ MAb molecules that did not previously bind to LDL in the serum, bound to the LDL coating the plate. The quantity of HB$_3$cB$_3$ MAb that was bound to LDL on the plate was inversely proportional to the concentration of LDL in the serum sample. After washing off the unbound components, bound HB$_3$cB$_3$ was detected using peroxidase-labeled anti-mouse IgG and the chromogenic (ABTS) peroxidase substrate (Kirkegaard and Perry Laboratories, Gaithersburg, Md.). Intensity of developed color was determined using an ELISA plate reader MR 580 (Dynatech, Chantilly, Va.). Dilutions of pure LDL (isolated by ultracentrifugation, see Alaupovic, P. et al., Biochim. Biophys. Acta, 260: 689–707 (1972), incorporated herein by reference) with known concentrations of ApoB-100 were used on each plate to construct a standard curve from which the concentrations of LDL-Apo B in the serum samples were calculated. The LDL-cholesterol concentrations were determined in the same sera using the LDL-DIRECT™ commercial kit (Sigma, St. Louis, Mo.). This method was used because it allows for an accurate determination of LDL-C even in sera with triglycerides as high as 1139 mg/dl.

Based on analysis of 100 human sera with variable lipoprotein profiles, the correlation between LDL-Apo B values determined by the $HB_3cB_3$ ELISA and LDL-cholesterol values determined by the commercial kit was highly significant. The correlation coefficient was 0.94 and corresponding P value was <0.0001. Twenty-six of these sera contained very high levels of triglycerides (400 to 1125 mg/dl), and were therefore rich in VLDL. However, the presence of excess VLDL did not interfere with the selective recognition of LDL by the $HB_3cB_3$ MAb. The correlation between LDL-Apo B determined by the $HB_3cB_3$ ELISA and the LDL-C determined by the commercial kit (Sigma, St. Louis, Mo.) was highly significant (r=0.93, p<0.0001)) even in this subgroup of twenty-six hyper-triglyceridemic sera.

The above data clearly indicated that $HB_3cB_3$ MAb recognizes an epitope of Apo B-100 that is fully expressed only on LDL particles. The $HB_3cB_3$ hybridoma cells producing the antibody were deposited in the American Type Culture Collection (12301 Parklawn Drive, Rockville, Md. 20852) under the ATCC designation number HB11612 on Apr. 8, 1994.

EXAMPLE 3

Preparation of Anti-LDL and Anti-HDL Dipsticks to Assay Human Serum, Plasma and Whole Blood To prepare dipsticks for analyses of LDL and HDL in human whole blood, serum and plasma samples, PVDF membrane (Bio-Rad, Hercules, Calif.) was treated with methanol and washed with water according to manufacturer's instructions. Washed membrane was cut into strips (5×60 mm) and stored in phosphate buffered saline (Sigma, St. Louis, Mo.) pH 7.4 at 4° C. The strips were incubated with the anti-LDL MAb $HB_3cB_3$ or the anti-HDL MAb $AlbD_5$ in PBS. Both of these MAbs were adjusted to the concentration of 1 mg/ml. Each strip was incubated in 6 ml of an antibody solution for 24 hours at 4° C. followed by two additional 24-hour incubations using fresh antibody solutions each time to adsorb MAbs to each strip. The purpose of these sequential incubations was to saturate strips with adsorbed antibodies. This was accomplished by the three consecutive incubations as indicated by the concentrations of antibodies left in solution after each incubation with PVDF strips. Coating of strips with MAbs was followed by an incubation in a 2% solution of nonfat milk proteins in PBS (Kirkegaard and Perry Laboratories, Gaithersburg, Md.) for 24 hours at 4° C. to block areas of PVDF not occupied by antibody molecules. After three washes in 30 ml of PBS, the strips were kept in PBS at 4° C. up to two weeks without noticeable loss of activity. Antibody-coated and blocked strips were also immersed in PBS containing 50 percent sucrose (Sigma, St. Louis, Mo.) for 5 minutes and sealed in small plastic bags. The sealed dipsticks retained their capacity to bind lipoproteins for up to twelve weeks at 4° C.

EXAMPLE 4

Use of Dipsticks to Assay LDL and HDL by Lipid Staining and Comparison to Other Assay Method Samples of human blood serum or plasma were diluted with 0.5% EDTA solution by adding 100 µl of EDTA to 100 µl of sample in an 0.5 ml plastic tube. A small piece of antibody-coated dipstick (5×5 mm) was immersed into diluted serum for 2 minutes at room temperature. The tube was shaken occasionally two to three times. This was followed by washing off unbound constituents of serum with tap water for 1 minute. The strip was then gently blotted against paper tissue to remove excess water and air dried for 2 minutes. Washing and drying was followed by staining of the strip in 200 µl of 0.02% Sudan Red 7B (Sigma, St. Louis, Mo.) dissolved in a mixture of methanol and 0.1 M NaOH (5:1 volume: volume) for 3 minutes with occasional shaking. The staining was followed by washing under the tap water for 1 minute, blotting and air drying for 5 minutes. A dipstick coated with no antibody and blocked with nonfat milk proteins served as a negative control. The whole procedure lasted approximately 15 minutes and was carried out at room temperature. Sudan Red 7B stained the lipid moiety of lipoproteins (LDL and HDL, respectively) captured on the antibody-coated strips. The intensity of color was clearly proportional to concentrations of LDL and HDL cholesterol determined in each serum by the respective conventional methods (Sigma, St. Louis, Mo.), as shown in Tables 4 and 5 below.

In Table 4, serum LDL-cholesterol was determined in all samples by a direct LDL-C assay (Sigma, St. Louis, Mo.). The same serum samples also were incubated with anti-LDL dipsticks and stained with Sudan Red 7B as described above. The color intensity was assessed visually (on an arbitrary scale of 1 to 15) by three individuals (I, II and III) presented with the complete set of 16 dipsticks at the same time. The averaged score of the color intensity correlated significantly with LDL-C concentrations (r=0.97, p<0.0001).

TABLE 4

Correlation between the serum LDL-cholesterol concentration and the color intensity of $HB_3cB_3$ coated (anti-LDL) dipsticks stained with Sudan Red 7B.

| Sample number | Serum LDL-cholesterol (mg/dl) | Dipstick color intensity | | | Average Average color score |
|---|---|---|---|---|---|
| | | I | II | III | |
| 1 | 145 | 4 | 4 | 4 | 4.0 |
| 2 | 130 | 4 | 4 | 3 | 3.7 |
| 3 | 97 | 2 | 2 | 2 | 2.0 |
| 4 | 165 | 6 | 5 | 4 | 5.0 |
| 5 | 115 | 3 | 2 | 2 | 2.3 |
| 6 | 200 | 8 | 10 | 9 | 9.0 |
| 7 | 207 | 8 | 8 | 9 | 8.3 |
| 8 | 160 | 6 | 5 | 5 | 5.3 |
| 9 | 115 | 2 | 3 | 2 | 3.3 |
| 10 | 276 | 15 | 15 | 15 | 15.0 |
| 11 | 155 | 6 | 5 | 5 | 5.3 |
| 12 | 98 | 2 | 1 | 1 | 1.3 |
| 13 | 123 | 3 | 3 | 3 | 3.0 |
| 14 | 130 | 3 | 4 | 2 | 3.0 |
| 15 | 185 | 6 | 6 | 7 | 6.3 |
| 16 | 73 | 1 | 1 | 1 | 1.0 |

In Table 5, serum HDL-cholesterol was determined in all samples by Sigma's HDL-C kit. The same serum samples were incubated with anti-HDL dipsticks and stained with Sudan Red 7B as described above. The color intensity was assessed visually (on an arbitrary scale of 1 to 10) by three individuals (I, II and III) presented with the complete set of 9 dipsticks at the same time. The averaged score of the color intensity correlated significantly with HDL-C concentrations (r=0.93, p<0.0005)

TABLE 5

Correlation between the serum HDL-cholesterol concentration and the color intensity of AIbD$_5$ coated (anti-HDL) dipsticks stained with Sudan Red 7B.

| Sample number | Serum LDL-cholesterol (mg/dl) | Dipstick color intensity | | | Average Average color score |
|---|---|---|---|---|---|
| | | I | II | III | |
| 1 | 65 | 10 | 10 | 10 | 10.0 |
| 2 | 53 | 6 | 6 | 6 | 6.0 |
| 3 | 58 | 5 | 6 | 6 | 5.7 |
| 4 | 48 | 5 | 5 | 6 | 5.3 |
| 5 | 40 | 5 | 6 | 5 | 5.3 |
| 6 | 60 | 7 | 8 | 8 | 7.7 |
| 7 | 28 | 1 | 1 | 1 | 1.0 |
| 8 | 37 | 3 | 3 | 3 | 3.0 |
| 9 | 39 | 3 | 3 | 3 | 3.0 |

Two other lipid stains, Oil Red 0 and Sudan Black B, gave similar results. All of these stains are commonly used for staining of lipoproteins in electrophoretic analyses of serum (Stein E. A. and Meyers, G. L., Lipids, Lipoproteins and Apolipoproteins, In *Tietz Textbook of Clinical Chemistry*, W. B. Saunders, Philadelphia pp 1002–1093 (1994)). The color on dipsticks is stable for fourteen days. Anti-LDL dipsticks were more intensely colored than anti-HDL dipsticks which reflects higher lipid content per LDL particle. The above experiments were also carried out with human plasma and serum with identical results. The total time to run the dipstick assay, from insertion into a blood sample to development of color is approximately 15 minutes.

EXAMPLE 5
Stability of Dipsticks and Lipid Stains

Anti-LDL and anti-HDL dipsticks were stored in 50 percent sucrose in sealed plastic bags for 3, 6 and 12 weeks at 4° C. as described above. Dipsticks were washed under the tap water for 1 minute and used immediately after removal from plastic bags. Incubations with serum and staining were carried out as described above at each of the indicated time intervals. To avoid storage-related decline in serum lipoproteins concentrations, aliquots of serum were stored at −70° C. and thawed at indicated time intervals immediately prior to experiments with dipsticks. There were no noticeable differences between anti-LDL dipsticks stored for various times over a period of twelve weeks. Similar results were obtained with anti-HDL dipsticks. All three lipid stains (Sudan Red 7B, Sudan Black B and Oil Red 0) dissolved in methanol were stable for four months at room temperature as well as 4° C. However, the 0.1 M NaOH solution, which is present in each staining solution, must be added immediately prior to staining the dipsticks to assure optimal and reproducible results.

EXAMPLE 6
Use of the Avidin-Biotin Complex to Bind Antibody to Dipsticks

The avidin-biotin system was also used to bind antibody molecules to PVDF strips. PVDF strips were incubated with egg-yolk avidin (Sigma, St. Louis, Mo.) dissolved in PBS (3 mg/ml) for 24 hours at 4° C. This step was repeated for a total of three times using fresh avidin solution each time. Strips were then blocked with 2% nonfat milk for 24 hours at 4° C. The strips were then incubated three times for 24 hours at 4° C. in a solution of biotinylated anti-LDL HB$_3$cB$_3$ MAb (1 mg/ml). The anti-LDL MAb was biotinylated at its Fc fragment using the periodate-biotin- LC-hydrazide technique (Pierce, Rockford, Ill.) which covalently couples biotin molecules to carbohydrate residues concentrated at the Fc portion of the antibody molecule. Biotinylation carried out in this fashion leaves the antigen combining sites of an antibody intact. Furthermore, with the Fc portion of the antibody attached to the layer of avidin on the strip, the antigen-binding sites are free to bind the antigen.

The avidin-biotin anti-LDL strips made with the avidin-biotin complex were kept in PBS at 4° C. These anti-LDL dipsticks made with avidin-biotin complexes stained more intensely than dipsticks coated with non-biotinylated anti-LDL. Each avidin molecule consisting of four subunits can bind four biotin molecules and the affinity of binding between these two molecules is extremely high (Savage, M. D. et al. *Avidin-Biotin Chemistry:* A Handbook, Pierce Chemical Company, Rockford, Ill. (1992)). Thus, anti-LDL dipsticks made with avidin-biotin complexes exhibited a higher LDL binding capacity than dipsticks made without the avidin-biotin system to bind antibody to the dipsticks.

EXAMPLE 7
Dipstick Method to Assay LDL by staining of Apolipoprotein B

The Pan B D$_6$ MAb is specific for Apo B and binds equally well to all Apo B-containing lipoproteins including LDL. The binding of Pan B (D$_6$) MAb to LDL does not interfere with the binding of HB$_3$cB$_3$ MAb to LDL. D$_6$ binds to the amino terminal half of Apo B–100 whereas HB$_3$cB$_3$ binds to the carboxy terminal end of B–100. Thus, both MAbs can bind simultaneously to the same LDL particle due to sufficient steric distance between their corresponding epitopes. The Pan B (D$_6$) Mab, biotinylated at the Fc fragment as described above, was mixed with streptavidin-peroxidase (BRL, Bethesda, Md.) to form antibody-peroxidase complex due to binding between the biotin on the antibody and the streptavidin conjugated to peroxidase. The complex was dialyzed against PBS containing 25% sucrose (Sigma, St. Louis, Mo.). This peroxidase-tagged Pan B (D$_6$) MAb complex was still capable of recognizing and binding to LDL. PVDF strips were coated with anti-LDL antibody (HB$_3$cB$_3$) and blocked as described above. Anti-LDL dipsticks were incubated with human serum samples for 2 minutes, washed under tap water, air dried for 2 minutes and incubated with biotinylated Pan B (D$_6$) MAb and streptavidin-peroxidase for 10 minutes. After the incubation with the Pan B (D$_6$) MAb-peroxidase complex, the dipsticks were washed with tap water and incubated for 2 minutes with the chromogenic peroxidase substrate TMB (Kirkegaard and Perry Laboratories, Gaithersburg, Md.). This was followed by an additional 1-minute washing under tap water and drying at room temperature for 5 minutes. The Pan (D$_6$) MAb-peroxidase complex bound to LDL captured by the anti-LDL strip and converted TMB substrate into a colored compound. The whole procedure was carried out at room temperature. The intensity of the blue-green color of dipsticks was proportional to the concentrations of LDL-cholesterol in the respective serum samples as shown by the data in Table 6 below.

In Table 6, serum LDL-C was determined in all samples by direct LDL-C assay (Sigma, St. Louis, Mo.). The same serum samples were incubated with anti-LDL dipsticks followed by incubation with D$_6$ MAb-peroxidase and staining with TMB substrate as described above. The color intensity was assessed visually (on an arbitrary scale of 1 to 15) by three individuals (I, II and III) presented with the complete set of 16 dipsticks at the same time. The averaged score of the color intensity correlated significantly with LDL-C concentrations (r=0.98, p<0.0001).

TABLE 6

Correlation between the serum LDL-cholesterol concentration and the color intensity of $HB_3cB_3$ coated (anti-LDL) dipsticks stained with $D_6$ MAb-peroxidase-TMB system.

| Sample number | Serum LDL-cholesterol (mg/dl) | Dipstick color intensity | | | Average Average color score |
|---|---|---|---|---|---|
| | | I | II | III | |
| 1 | 145 | 5 | 4 | 4 | 4.3 |
| 2 | 130 | 4 | 3 | 5 | 4.0 |
| 3 | 97 | 2 | 2 | 3 | 2.3 |
| 4 | 165 | 7 | 7 | 6 | 6.7 |
| 5 | 115 | 3 | 2 | 3 | 2.7 |
| 6 | 200 | 8 | 9 | 9 | 8.7 |
| 7 | 207 | 8 | 9 | 9 | 8.7 |
| 8 | 160 | 5 | 6 | 7 | 5.7 |
| 9 | 115 | 2 | 2 | 2 | 2.0 |
| 10 | 276 | 15 | 15 | 15 | 15.0 |
| 11 | 155 | 6 | 4 | 4 | 4.7 |
| 12 | 98 | 1 | 2 | 2 | 1.7 |
| 13 | 123 | 3 | 3 | 3 | 3.0 |
| 14 | 130 | 3 | 4 | 4 | 3.7 |
| 15 | 185 | 6 | 6 | 9 | 7.0 |
| 16 | 73 | 1 | 1 | 1 | 1.0 |

To summarize, the above experiments demonstrated that anti-LDL dipsticks allow for quantification of LDL by visualizing either lipids by staining with lipid stains or Apo-B by staining with a protein stain or chromogenic assay using a substrate such as TMB.

EXAMPLE 8

Dipstick Method to Assay HDL by Staining of Apolipoprotein A-I

Anti-HDL dipsticks coated with AIbD, MAb were used to adsorb HDL particles in human serum samples as described above. After washing, the dipsticks were incubated with the second MAb to Apo-I ($AIbE_2$) complexed with streptavidin peroxidase as described above. The $AIbE_2$-peroxidase complex bound to the HDL particles which were captured on the dipstick by the $AIbD_5$ MAb. After incubation with TMB, washing, and drying, the color intensity was proportional to the serum HDL cholesterol as shown by the data in Table 7 below.

In Table 7, serum HDL-cholesterol was determined in all samples by a commercial kit (Sigma, St. Louis, Mo.). The same serum samples were incubated with anti-HDL dipsticks followed by incubation with $AIbE_2$ MAb-peroxidase complex and staining with TMB as described above. The color intensity was assessed visually (on an arbitrary scale of 1 to 10) by three individuals (I, II and III) presented with the complete set of 9 dipsticks at the same time. The averaged score of the color intensity correlated significantly with HDL-C concentrations (r=0.97, p<0.0001)

TABLE 6

Correlation between the serum HDL-cholesterol concentration and the color intensity of $AIbD_5$ (anti-HDL) dipsticks stained with $AIbE_2$ MAb-peroxidase-TMB system

| Sample number | Serum LDL-cholesterol (mg/dl) | Dipstick color intensity | | | Average Average color score |
|---|---|---|---|---|---|
| | | I | II | III | |
| 1 | 65 | 10 | 10 | 10 | 10.0 |
| 2 | 53 | 6 | 7 | 6 | 6.3 |
| 3 | 58 | 6 | 7 | 7 | 6.7 |
| 4 | 48 | 6 | 5 | 5 | 5.3 |
| 5 | 40 | 5 | 4 | 5 | 4.7 |
| 6 | 60 | 8 | 8 | 8 | 8.0 |
| 7 | 28 | 1 | 1 | 1 | 1.0 |
| 8 | 37 | 4 | 4 | 4 | 4.0 |
| 9 | 39 | 4 | 4 | 4 | 4.0 |

Both Pan B ($D_6$) MAb- and $AIbE_2$MAb-peroxidase complexes were stable in PBS containing 25% sucrose for at least 3 months at 4° C.

EXAMPLE 9

Dipstick Method to Assay the LDL/HDL Ratio

Anti-LDL and anti-HDL dipsticks, prepared as described above, were used to determine the relative ratio of LDL-Apo B to HDL-Apo A-I, that is, the LDL/HDL ratio. Small pieces (0.5×0.5 cm) of both anti-HDL and anti-LDL dipsticks were simultaneously incubated with the same sample of human serum, plasma, or whole blood for 2 minutes, washed under tap water, air dried for 2 minutes and incubated with an equimolar mixture of $D_6$ MAb- and $AIbE_2$ MAb-streptavidin-peroxidase complexes for 10 minutes to detect bound LDL and HDL, respectively. This was followed by washing under tap water, a 2-minute air drying, and a 2-minute incubation with the TMB substrate as described above. After an additional washing under tap water and air drying at room temperature (5 minutes) the color intensity on both dipsticks was compared visually. The serum, plasma or blood samples with known concentrations of HDL-cholesterol (HDL-C) and LDL-cholesterol (LDL-C) were analyzed by the above dipstick method. Sera with LDL-C concentrations between 110 mg/dl and 130 mg/dl and HDL-C concentrations between 40 and 55 mg/dl showed comparable color intensity on both dipsticks. Sera with LDL-C values higher than 140 mg/dl generally show more intense color on anti-LDL dipsticks. The only exceptions were the sera with HDL-C levels higher than 50 mg/dl. In these cases, anti-HDL dipsticks tended to be more intensely stained unless the LDL-C levels exceeded 160 mg/dl.

Virtually identical results were obtained when anti-HDL and anti-LDL dipsticks were used separately. In these experiments each serum with previously determined HDL-C and LDL-C was separately incubated with anti-HDL and anti-LDL dipsticks and stained with $AIbE_2$ and $D_6$ MAb-peroxidase complexes, respectively. The agreement between these two types of experiments demonstrates that even in case of simultaneous incubation of anti-HDL and anti-LDL dipsticks with the same serum, plasma or blood sample followed by the simultaneous incubation of both dipsticks with the mixture of $AIbE_2$ MAb- and $D_6$ MAB-peroxidase, the reactions between lipoproteins and corresponding MAbs coated on the dipsticks remain specific. HDL particles always bind to the $AIbD_5$ MAb coating the anti-HDL dipstick and the $AIbE_2$ MAb-peroxidase complex binds to the HDL-Apo A-I captured by the anti-HDL dipstick. The same is true for LDL particles which bind exclusively to the HB$_3$cB$_3$ MAb coating the anti-LDL dipstick and react with the D$_6$ MAb-peroxidase complex.

These studies demonstrate that the dipstick methodology provides a quick and simultaneous determination of relative quantities of HDL and LDL in serum, plasma, or whole blood samples. To determine the LDL/HDL ratio in an unknown blood sample, the color intensities on the HDL and LDL dipsticks, which were incubated with the unknown sample, are compared to a set of printed color standards derived from blood samples with known LDL/HDL ratios.

EXAMPLE 10
Dipstick Method to Assay LPA-I/LPA-I:A-II Ratio

To determine the LP A-I/LP A-I:A-II ratio, two dipsticks were used. One of them was coated with AlbD$_5$ MAb (anti-Apo A-I) and the other with CdB$_5$ MAb (anti- Apo A-II). In addition to these two MAbs, a third MAb, AlbE$_2$ (anti-Apo A-I) was also used. AlbE$_2$ was biotinylated at the Fc portion of IgG molecule and complexed with streptavidin-peroxidase as described above. Samples of EDTA treated whole blood, serum and plasma were simultaneously incubated with both anti-Apo A-I and anti-Apo A-II dipsticks for 2 minutes at room temperature. Dipsticks were then washed under tap water, incubated with the AlbE$_2$ MAb-peroxidase complex for 10 minutes, washed again, incubated with TMB substrate, washed and air dried as described above. Intensities of the blue-green color developed on both dipsticks were compared visually. The dipstick coated with AlbD$_5$ MAb (anti-Apo A-I) captured both LP A-I and LP A-I:A-II particles, and it was always more intensely stained relative to the CdB$_5$ (anti-Apo A-II) coated dipstick. The latter dipstick captures only LP A- I:A-II subfraction which represents approximately 60% of all Apo A-I-containing particles (Koren, E. et al. Clin. Chem., 33:38–43 (1987)). However, there were clear differences between various blood samples.

For example, in males, the difference between AlbD$_5$ (anti-Apo A-I) dipsticks and the CdB$_5$ (anti-Apo A-II) dipsticks,although present, were generally less noticeable due to somewhat weaker staining of the anti-Apo A-I dipsticks. In females, AlbD$_5$ dipsticks were usually more intensely stained relative to CdB$_5$ coated dipsticks, reflecting higher concentrations of Lp A-I in their blood (Koren, E. et al., Clin. Chem., 33:38–43 (1987)). In addition to these observations, there was a good correlation between the relative color intensities of both dipsticks and their respective particles determined by the ELISA described by Koren, E. et al. *Clin. Chem.* 33:38–43 (1987), incorporated herein by reference. These experiments demonstrate that the dipstick methodology can be successfully used for a quick determination of LP A-I/LP A-I:A-II ratio. To determine the LP A-I/LP A-I:AII ratio in an unknown blood sample, the color intensities of the anti-Apo A-I and anti-Apo A-II dipsticks which were incubated with the unknown sample are compared to a set of printed color standards derived from dipsticks incubated with blood samples with known concentrations of LP A-I and LP A-I:A-II.

EXAMPLE 11
Dipstick Method to Assay the Distribution of Apo C-III and Apo-E (C-III ratio and E ratio)

The "C-III Ratio" has been shown to be a reliable indicator of the progression of coronary artery disease (Alaupovic, P. and Blankenhorn, D. H. *Klin. Wochenschr.,* 60:38–40 (1990); Blankenhorn, D. H. et al. *Circulation,* 81:470–478 (1990)). The current methodology for the C-III ratio is based on precipitation of all Apo B-containing lipoprotein particles with heparin and quantification of Apo C-III in both the heparin precipitate and heparin supernatant fraction. The Apo C-III in the heparin precipitate fraction represents Apo C-III associated with Apo B in VLDL and VLDL remnant particles. Apo C-III remaining in the supernatant fraction is associated with HDL particles. The C-III ratio is calculated by dividing the Apo C-III in the heparin supernatant by the Apo C-III in the heparin precipitate. A low C-III ratio is associated with progression of coronary disease.

The dipstick methodology described above was also used to determine the distribution of Apo C-III, that is, to obtain a C-III ratio. PVDF strips were coated with the Pan B (D$_6$) MAb, blocked and incubated with human serum plasma or whole blood as described above. This was followed by washing, an incubation with the XbA$_3$ (anti-Apo C-III) MAb-peroxidase complex, an additional washing, and an incubation with chromogenic TMB substrate as described above. The color developed on the Pan B (D$_6$) MAb-coated dipsticks was proportional to the Apo C-III associated with Apo B. As described earlier, the Pan B (D$_6$) MAb binds all Apo B-containing particles, including LDL. However, the amount of Apo C-III associated with Apo B in LDL is negligible. Therefore, the color intensity on the Pan B coated dipsticks reflected the amount of Apo C-III associated with VLDL and VLDL remnant particles. The anti-Apo A-I (or anti-HDL) dipsticks coated with AlbD$_5$MAb were also used in combination with the XbA$_3$ MAb-peroxidase complex. The color on these dipsticks was proportional to the amount of Apo C-III associated with Apo A-I in HDL particles.

A visual comparison of the Pan B and the anti-HDL dipsticks after incubation with the same serum sample and staining, allowed for an estimation of the C-III ratio. A serum with a high C-III ratio (as determined by assaying C-III in a heparin supernatant and precipitate) showed relatively strong color on the anti-HDL dipstick and only a faint color on the Pan B (D$_6$) MAb dipstick. A serum, which was previously shown to have a low C-III ratio, showed more intense color on the Pan B (D$_6$) MAb dipstick and relatively weak color on the anti-HDL MAb dipstick. Identical results were obtained with whole blood.

Similar experiments were carried out to determine the Apo E ratio by the use of appropriate dipsticks. As described above, the Apo E ratio is determined by dividing Apo E in heparin supernate with the Apo E in heparin precipitate. The Apo E ratio is analogous to the C-III ratio and reflects the quantity of VLDL and their remnants relative to the HDL particles. To determine the Apo E ratio, the Pan B and anti-HDL dipsticks (coated with D$_6$ and AlbD$_5$ MAbs, respectively) were incubated with human serum, plasma or whole blood for 2 minutes, washed under tap water, air dried for 2 minutes and incubated with an equimolar mixture of two anti-Apo E MAbs (each complexed with streptavidin-peroxidase) for 10 minutes. This was followed by washing and incubation with TMB substrate as described above. Two anti-Apo E MAbs (EfB, and EfD$_3$) were separately biotinylated at their Fc fragments and complexed with the streptavidin-peroxidase as described above. Since EfB, MAb binds predominantly to Apo E associated with VLDL, whereas EfD$_3$ preferentially binds Apo E on HDL particles, an equimolar mixture of EfB, and EfD$_3$-peroxidase complexes was used for incubation with the Pan B and anti-HDL dipsticks. This mixture was used in place of a single MAb with equal binding to all Apo E-containing lipoproteins. Nevertheless, determination of the Apo E ratio with the above dipsticks is quite similar to the Apo C-III ratio. The sera with low Apo E ratio determined by the heparin precipitation method gave a relatively weak staining on anti-HDL dipsticks, reflecting a low concentration of Apo E associated with Apo A-I in HDL particles, and an intense staining on the Pan B dipsticks due to the high concentration of Apo E associated with Apo B. The sera with high Apo E ratio gave an inverse pattern (strong staining of anti-HDL and weaker staining of Pan B dipsticks).

These experiments demonstrate that a dipstick technique using described combinations of MAbs to apolipoproteins A-I, B, C-III and E provides a quick (approximately 30 minutes) estimation of the C-III and E ratios in human serum, plasma and whole blood, or other biological samples. The conventional determinations of these ratios cannot be done with whole blood and take 12–24 hours (Alaupovic, P. Can. J. Biochem., 59:565–579 (1981)).

EXAMPLE 12
Production of Recombinant Anti-LDL Antibody

Murine hybridoma cells producing anti-LDL $HB_3cB_3$ MAb were used to produce recombinant anti-LDL using a commercially available recombinant phage antibody system (RPAS, Pharmacia Biotech Inc., Piscataway, N.J.). Briefly, mRNA was isolated from $HB_3cB_3$ producing hybridoma cells, followed by synthesis of cDNA encoding the variable regions of both heavy and light chains of the $HB_3cB_3$ MAb. The heavy and light chain encoding cDNAs were amplified in two separate PCRs using two sets of primers, specific for each chain. The amplified heavy and light chain cDNA fragments were then purified using agarose gel electrophoresis and assembled into a single recombinant DNA fragment using a DNA linker fragment (Pharmacia Biotech Inc., Piscataway, N.J.). The resulting recombinant DNA molecule encodes a single chain polypeptide, called a single chain Fv fragment (ScFv), which binds the same epitope as the original MAb.

The recombinant DNA fragment was approximately 700 base pairs in length. The assembled ScFv DNA was amplified with a set of oligonucleotide primers that introduced the SfiI and NotI restriction sites. This recombinant DNA fragment was further purified and sequentially digested with SfiI and NotI to generate cohesive ends for ligation into the phage plasmid (phagemid) pCANTAB 5 (Pharmacia Biotech Inc., Piscataway, N.J.) cloning vector. The inserted recombinant DNA encoding the ScFv was fused with the 5' end of the gene coding the g3p minor coat protein located at the tip of the phage. The ligated phagemid vector containing the inserted DNA, was introduced into competent E. coli TG 1 cells.

Phagemid-containing bacterial colonies were infected with M13 KO7 helper phage to yield recombinant phage which display ScFv antibodies. At this stage, recombinant anti-LDL ScFv antibody is expressed on the tip of the phage as a fusion product between the antigen-binding site of $HB_3cB_3$ MAb and the M13 g3p minor coat protein. Phage, containing phage-displayed ScFv antibodies capable of binding LDL, were selected by panning in LDL-coated cell culture flasks. The panning and reinfection of E. coli TG 1 cells was repeated several times until phage-displayed ScFv antibodies of high affinity were obtained. The LDL binding affinity of the ScFv antibodies was determined using an ELISA method. The wells of microtiter ELISA plates were coated with serial dilutions (80 to 2.5 µg/ml) of LDL and blocked as described above. Phage displaying anti-LDL ScFv antibodies were pipetted into duplicate wells and allowed to bind for 3 hours at room temperature (approximately 25° C.). After washing, the peroxidase-labelled sheep antibody directed against the M13 g8p major coat protein was added to detect the presence of recombinant phage antibodies bound to LDL. After washing, a peroxidase chromogenic substrate (ABTS, Kirkegaard and Perry Laboratories, Gaithersburg, Md.) was added and the resulting color intensity measured by the use of an ELISA plate reader (MR 580, Dynatech Chantilly, Va.). The serial dilutions of LDL gave rise to a binding curve for each recombinant phage anti-LDL. The slopes of binding curves were compared to the slope of the native anti-LDL $HB_3cB_3$ MAb which was used on each plate as a positive control. Out of 35 phage ScFv antibodies, several showed affinities comparable to $HB_3cB_3$ MAb based on the slopes of binding curves as shown in Table 8.

In Table 8, ELISA plates were coated with LDL using concentrations indicated in the left column. LDL coated wells were incubated (in duplicates) with $HB_3cB_3$ MAb (2 µg/ml) and $RcB_3M_1D_4$ recombinant phage antibody as described above. Detection of bound antibodies was carried out using the respective peroxidase labeled conjugates as described above. The numbers represent average optical density readings values from two separate experiments.

TABLE 8

Binding of $HB_3cB_3$ MAb (anti-LDL) and $RcB_3M_1D_4$ recombinant phage antibody to LDL

| LDL concentration µg protein/ml | $HB_3cB_3$ monoclonal antibody | $RcB_3M_1D_4$ recombinant Phage antibody |
|---|---|---|
| 80 | 0.802 | 0.675 |
| 40 | 0.497 | 0.406 |
| 20 | 0.263 | 0.211 |
| 10 | 0.115 | 0.098 |
| 5 | 0.060 | 0.047 |
| 2.5 | 0.042 | 0.036 |

ScFv phage antibody with the highest affinity ($RcB_3M_1D_4$) was placed on deposit at the American Type Culture Collection (12301 Parklawn Drive, Rockville, Md. 20852) under the ATCC designation number 69602.

EXAMPLE 13
Use of Recombinant Phage Anti-LDL ScFv Antibodies to Detect LDL

Intact phage displaying the recombinant anti-LDL ScFv antibody $RCB_3M,D_4$ were used in both ELISA and dipstick methods to detect LDL. ELISA microtiter plates were coated with a sheep antibody to M13 g8p coat protein (Pharmacia Biotech Inc., Piscataway, N.J.) and blocked with a 0.1% nonfat milk proteins as described above. After washing, the recombinant phage anti-LDL ScFv antibodies were added to the plate and allowed to bind to the anti-M13 g8p antibody overnight at 4° C. Because the anti-LDL ScFv antibody is expressed on the tip of the phage as a protein fused to the minor coat g3p protein, the anti-LDL binding site is free to bind LDL. Unbound recombinant phages were washed off and the wells incubated with dilutions of LDL (3 hours at room temperature). The unbound LDL was then washed away, and the Pan B ($D_6$) MAb antibody-peroxidase complex was added and incubated as described above. Unbound Pan B ($D_6$) MAb was washed away and the chromogenic peroxidase substrate (ABTS) was added. The color intensity in each well was read using an ELISA plate reader. The color intensity correlated with the concentration of LDL used in each well of the plates. The negative control wells coated with the native M13 phage showed no color at all.

The phage anti-LDL ScFv antibody $RcB_3M_1D_4$ was also used to explore its suitability for the dipsticks. PVDF strips were sequentially coated with the anti-g8p antibody and blocked with 2% nonfat milk proteins as described above. This was followed by three sequential 24-hour incubations of the strips in a solution of $RcB_3M_1D_4$ phage antibody at 4° C. After washing in PBS, strips were incubated with LDL dilutions followed by an incubation with the Pan B ($D_6$) MAb-peroxidase complex, washing, and incubation in TMB chromogenic substrate as described above for the $HB_3cB_3$ MAb dipsticks. The intensity of color on the phage anti-LDL ScFv antibody-coated dipsticks was proportional to the concentration of LDL. The experiments with the phage anti-LDL demonstrate that the recombinant anti-LDL ScFv antibodies are capable of binding to LDL under the conditions used in described ELISA as well as dipstick methods. Thus, anti-LDL ScFv antibodies made free of the phage components (Hoogenboom, H. R. et al. *Nucl. Acid. Res.* 19:4133–4137 (1991)) are likewise suitable, for use in methods and compositions such as ELISA and dipstick methodologies described above.

The rest of the hybridomas described above, which which produce the corresponding MAbs: $AIbD_5$, $AIbE_2$, $CdB_5$, $XbA_3$, $EfB_1$, $EfD_3$, are also useful to create a library of corresponding recombinant antibodies. This approach offers several important advantages. ScFv-encoding DNA recombinant molecules have also been produced from cDNA of the $AIbD_5$ and $D_6$ hybridomas and can be inserted into pCANTAB5 for making recombinant antigen-specific antibodies such as the $RcB_3M_1D_4$ anti-LDL recombinant phage antibody described above.

Modifications and variations of the present invention will be obvious to those skilled in the art from the foregoing detailed description. Such modifications and variations are intended to come within the scope of the appended claims.

We claim:

1. A method for determining the concentration of a specific lipoprotein, an apolipoprotein, or lipid associated with a specific lipoprotein, in a biological sample comprising:
   contacting the sample with antibody molecules immunoreactive with a specific lipoprotein or apolipoprotein, wherein the antibody molecules are selected from the group consisting of monoclonal antibodies, recombinant antibodies, and monoclonal antibody fragments that specifically bind to a stable, conformation independent epitope which is uninfluenced by the lipid content of the apoliprotein and lipoprotein molecule specifically bound by the antibody, wherein the molecule is selected from the group consisting of lipoproteins and apolipoproteins;
   under conditions wherein the antibody molecules can form an immune complex with lipoprotein or apolipoprotein in the sample; and
   determining the amount of lipoprotein, apolipoprotein, or lipid associated with a lipoprotein bound by the antibody molecules by detecting the amount of immune complex formed by binding of the antibody molecules with the lipoprotein or apolipoprotein in the sample.

2. The method of claim 1 wherein the antibody molecules are immunoreactive with a lipoprotein selected from the group consisting of HDL, LDL, and VLDL.

3. The method of claim 1 wherein the antibodies are monoclonal antibodies.

4. The method of claim 3, wherein the antibody is the anti-LDL monoclonal antibody produced by the hybridoma cell line $HB_3cB_3$ ATCC designation number HB 11612.

5. The method of claim 3, wherein the antibody is a recombinant anti-LDL $RcB_3M_1D_4$ ATCC designation number 69602.

6. The method of claim 1 wherein the antibody is immobilized on a solid substrate, the sample is contacted with the immobilized antibody, the unreacted sample is removed, and the amount of lipoprotein, apolipoprotein lipid is determined by staining of the material complexed with the immobilized antibody using a lipid stain.

7. The method of claim 6 wherein the lipid stain is selected from the group consisting of Sudan Red 7B, Oil Red O, and Sudan Black B.

8. The method of claim 6 wherein the lipoprotein lipid is stained prior to immunoreaction with the immobilized antibodies.

9. The method of claim 6, further comprising in solution antibody immunoreactive with apolipoprotein, wherein the anti-apolipoprotein antibody is coupled to a protein stain and used to stain lipoprotein in the sample, prior to immunoreaction of the sample with the immobilized antibodies which then bind to the stained antibody-bound apolipoprotein.

10. The method of claim 1, wherein the apolipoprotein is selected from the group consisting of Apo A-I, Apo A-II, Apo B, Apo C-III, and Apo E.

11. The method of claim 1, wherein the biological sample is selected from the group consisting of blood, plasma, and serum.

12. The method of claim 1 further comprising:
   contacting a first antibody immunoreactive with a specific apolipoprotein into the sample;
   allowing the antibody to complex with the apolipoprotein in the sample,
   adding to the sample a second antibody immunoreactive with a second, distinct epitope of the apolipoprotein,
   allowing the second antibody to bind to the apolipoprotein,
   detecting the presence of the apolipoprotein bound by both antibodies, and
   determining the amount of apolipoprotein bound by both antibodies.

13. The method of claim 12 wherein the apolipoprotein is apolipoprotein Apo B-100.

14. The method of claim 1 wherein the antibody specifically binds to an isoform of an apolipoprotein selected from the group consisting of Apo B-100, Apo B-48; Apo C-I, Apo C-II and Apo C-III.

15. The method of claim 14 wherein the isoform is Apo B-100.

16. A method for determining the concentration of a specific lipoprotein, an apolipoprotein, or lipid associated with a specific lipoprotein, in a biological sample, wherein the sample is a solution, comprising
   contacting the sample with a first antibody selected from the group consisting of monoclonal antibodies, recombinant antibodies, and antibody fragments that are immunoreactive with a stable, conformation independent epitope which is uninfluenced by the lipid content of a specific lipoprotein, apolipoprotein, and lipid associated with a specific lipoprotein under conditions wherein the first antibody molecules specifically complex with the epitope in the sample;
   adding to the sample a second antibody immunoreactive with a second, distinct epitope of the lipoprotein, apolipoprotein, or lipid associated with a specific lipoprotein, wherein the second antibody can form an immune precipitate with the complex of the first antibody and the specific lipoprotein, apolipoprotein, or lipid associated with a specific lipoprotein to be detected, in the biological sample which can be detected in the solution; and
   determining the amount of lipoprotein, apolipoprotein, or lipid associated with a lipoprotein in the sample bound by the first and second antibody molecules by detecting the amount of immune precipitate formed.

17. The method of claim 16 wherein the first antibody is an anti-LDL monoclonal antibody produced by the hybridoma cell line HB$_3$cB$_3$ ATCC designation number HB 11612.

18. The method of claim 17 wherein the second antibody is immunoreactive with apoprotein B and influenced by lipid or lipoprotein content in the sample.

19. The method of claim 18 wherein the lipid is present in low density lipoprotein.

20. A method for making a composition comprising immobilizing on a solid phase material antibody molecules immunoreactive with a specific lipoprotein or apolipoprotein, wherein the antibody molecules are selected from the group consisting of monoclonal antibodies, recombinant antibodies, and fragments thereof, and wherein the antibody has a binding affinity of at least $10^9$ for a stable, conformation independent epitope which is uninfluenced by the lipid content of the molecule selectively bound by the antibody, wherein the molecule is selected from the group consisting of lipoproteins and apolipoproteins.

21. The method according to claim 20 wherein the antibody molecule is specifically immunoreactive with LDL.

22. The method of claim 20 wherein the apolipoprotein is selected from the group consisting of Apo A-I, Apo A-II, Apo B, Apo C-III, and Apo E.

23. A composition for determining the concentration of a lipoprotein, apolipoprotein, or lipid associated with a single specific lipoprotein in a biological sample comprising:

monoclonal or recombinant antibody molecules specifically immunoreactive with a single specific lipoprotein or apolipoprotein, wherein the antibody molecules are selected from the group consisting of monoclonal antibodies, recombinant antibodies, and monoclonal antibody fragments that specifically bind to a stable, conformation independent epitope which is uninfluenced by the lipid content of the lipoprotein, apolipoprotein, and lipid associated with the specific lipoprotein.

24. The composition of claim 23 wherein the antibodies are monoclonal antibodies.

25. The composition of claim 23 wherein the antibody is the anti-LDL monoclonal antibody produced by the hybridoma cell line HB$_3$cB$_3$ ATCC designation number HB 11612.

26. The composition of claim 23 wherein the antibody is a recombinant anti-LDL RcB$_3$M$_1$D$_4$ ATCC designation number 69602.

27. The composition of claim 23 wherein the apolipoprotein is selected from the group consisting of Apo A-I, Apo A-II, Apo B, Apo C-III, and Apo E.

28. The composition of claim 23 wherein the antibody specifically binds to an isoform of an apolipoprotein selected from the group consisting of Apo B-100, Apo B-48; Apo C-I, Apo C-II and Apo C-III.

29. The composition of claim 28 wherein the isoform is Apo B-100.

30. A kit comprising the antibody of claim 23 further comprising a second monoclonal antibody immunoreactive with a second distinct epitope of the lipoprotein or apolipoprotein which is immunoreactive with the first antibody.

31. A kit comprising the antibody of claim 23 further comprising at least one internal standard comprising a known amount of a particular lipoprotien, lipoprotein lipid, or apolipoprotein.

* * * * *